United States Patent
Geva et al.

(10) Patent No.: US 11,478,618 B2
(45) Date of Patent: Oct. 25, 2022

(54) ULTRASONIC URINARY BLADDER DRUG DELIVERY

(71) Applicant: VENSICA MEDICAL LTD., M.P. Misgav (IL)

(72) Inventors: Avner Geva, Tel Aviv (IL); Leonid Kushkuley, Rehovot (IL)

(73) Assignee: VENSICA MEDICAL LTD., Tel Aviv (IL)

( * ) Notice: Subject to any disclaimer, the term of this patent is extended or adjusted under 35 U.S.C. 154(b) by 429 days.

(21) Appl. No.: 15/561,733

(22) PCT Filed: Mar. 25, 2016

(86) PCT No.: PCT/IL2016/050326
§ 371 (c)(1),
(2) Date: Sep. 26, 2017

(87) PCT Pub. No.: WO2016/151595
PCT Pub. Date: Sep. 29, 2016

(65) Prior Publication Data
US 2018/0104455 A1    Apr. 19, 2018

Related U.S. Application Data

(60) Provisional application No. 62/273,503, filed on Dec. 31, 2015, provisional application No. 62/203,109, (Continued)

(51) Int. Cl.
*A61M 25/00* (2006.01)
*A61M 25/10* (2013.01)
(Continued)

(52) U.S. Cl.
CPC ......... *A61M 25/10* (2013.01); *A61B 17/2202* (2013.01); *A61B 17/225* (2013.01);
(Continued)

(58) Field of Classification Search
CPC .......... A61M 25/10; A61M 2025/1086; A61M 2210/1085; A61M 2025/1085;
(Continued)

(56) References Cited

U.S. PATENT DOCUMENTS 5,749,845 A     5/1998  Hildebrand et al.
6,254,598 B1 *  7/2001  Edwards .................. A61N 1/40
                                                        606/41

(Continued)

FOREIGN PATENT DOCUMENTS

WO       2015014487 A1     2/2015

OTHER PUBLICATIONS

T. Terahara, "Dependence of low-frequency sonophoresis on ultrasound parameters; distance of the horn and intensity", International Journal of Pharmaceutics 235, 35-42, 2002.

(Continued)

*Primary Examiner* — Tiffany Legette-Thompson
(74) *Attorney, Agent, or Firm* — The Roy Gross Law Firm, LLC; Roy Gross

(57) ABSTRACT

A kit comprising: a urinary catheter comprising a first and a second longitudinal lumens; an ultrasonic transducer disposed about said catheter; a balloon mounted on said catheter, and enclosing said transducer; and a reservoir containing an acoustic coupling medium, wherein: said catheter further comprises a first opening in said first longitudinal lumen, said first opening disposed inside said balloon and configured to inflate said balloon with at least some of said acoustic coupling medium, said catheter further comprises a second opening in said second longitudinal lumen, said second opening disposed outside said balloon and configured to deliver a therapeutic fluid into the urinary bladder, around said balloon, and activation of said transducer in said urinary bladder causes cavitation bubbles to form in said (Continued)

therapeutic fluid adjacent an internal surface of the urinary bladder, and little or no cavitation bubbles are formed in said acoustic coupling medium in said balloon.

25 Claims, 18 Drawing Sheets

Related U.S. Application Data filed on Aug. 10, 2015, provisional application No. 62/138,573, filed on Mar. 26, 2015.

(51) Int. Cl.

| | | |
|---|---|---|
| *A61B 17/22* | (2006.01) | |
| *A61B 17/225* | (2006.01) | |
| *A61N 7/00* | (2006.01) | |
| *A61M 31/00* | (2006.01) | |
| *A61M 37/00* | (2006.01) | |
| *A61L 29/16* | (2006.01) | |
| *A61K 45/06* | (2006.01) | |

(52) U.S. Cl.
CPC .............. *A61L 29/16* (2013.01); *A61M 31/00* (2013.01); *A61M 31/002* (2013.01); *A61M 37/0092* (2013.01); *A61N 7/00* (2013.01); *A61B 2017/22007* (2013.01); *A61B 2017/22008* (2013.01); *A61B 2017/22082* (2013.01); *A61K 45/06* (2013.01); *A61M 2025/1086* (2013.01); *A61M 2210/1085* (2013.01); *A61N 2007/0039* (2013.01); *A61N 2007/0043* (2013.01)

(58) Field of Classification Search
CPC ................ A61M 31/00; A61M 31/002; A61M 37/0092; A61B 17/2022; A61B 17/225; A61B 2017/22082; A61B 2017/22008; A61B 2017/22007; A61B 201/22082; A61B 201/22008; A61B 201/22007; A61B 17/2202; A61N 7/00; A61N 2007/0043; A61N 2007/0039; A61K 45/06

See application file for complete search history.

(56) References Cited

U.S. PATENT DOCUMENTS

| | | | |
|---|---|---|---|
| 6,296,619 B1 | 10/2001 | Brisken et al. | |
| 7,927,836 B2 | 4/2011 | Doelle et al. | |
| 8,338,164 B2 | 12/2012 | Deem et al. | |
| 9,937,245 B2 | 4/2018 | Pfeil et al. | |
| 2003/0040712 A1* | 2/2003 | Ray | A61M 25/0084 604/173 |
| 2003/0092667 A1* | 5/2003 | Tachibana | A61K 41/0047 514/44 A |
| 2005/0228318 A1* | 10/2005 | Iger | A61N 7/00 601/2 |
| 2006/0184076 A1 | 8/2006 | Gill et al. | |
| 2008/0045882 A1* | 2/2008 | Finsterwald | A61M 37/0092 604/22 |
| 2008/0077056 A1* | 3/2008 | Kagosaki | A61B 8/00 601/2 |
| 2008/0249500 A1* | 10/2008 | Keith | A61M 25/0084 604/506 |
| 2009/0299327 A1* | 12/2009 | Tilson | A61M 25/1002 604/500 |
| 2011/0257523 A1 | 10/2011 | Hastings et al. | |
| 2012/0130288 A1* | 5/2012 | Holland | A61B 17/2202 601/2 |
| 2012/0226230 A1 | 9/2012 | Gerrans et al. | |
| 2012/0271167 A1 | 10/2012 | Holland et al. | |
| 2013/0023802 A1 | 1/2013 | McLntosh et al. | |
| 2013/0197555 A1* | 8/2013 | Schaer | A61N 7/00 606/170 |
| 2014/0039358 A1 | 2/2014 | Zhou et al. | |
| 2014/0275966 A1* | 9/2014 | Schwartz | A61B 8/08 600/411 |
| 2015/0164401 A1 | 6/2015 | Toth et al. | |

OTHER PUBLICATIONS

International Search Report of PCT/IL2016/050326 Completed Jul. 27, 2016; dated Jul. 28, 2017 7 Pages.
Written Opinion of ISR of PCT/IL2016/050326 Completed Jul. 27, 2016; dated Jul. 28, 2017 8 Pages.
Schurch et al., "Botulinum Toxin Type A is a Safe and Effective Treatment for Neurogenic Urinary Incontinence: Results of a Single Treatment, Randomized, Placebo Controlled 6-Month Study" The Journal of Urology vol. 174, pp. 196-200, (2005).

* cited by examiner

ULTRASONIC URINARY BLADDER DRUG DELIVERY

CROSS-REFERENCE TO RELATED APPLICATIONS

This application is a National Phase of PCT Patent Application No. PCT/IL2016/050326 having International filing date of Mar. 25, 2016, which claims the benefit of priority of U.S. Provisional Patent Application No. 62/138,573 filed Mar. 26, 2015, U.S. Provisional Patent Application No. 62/203,109 filed Aug. 10, 2015, and U.S. Provisional Patent Application No. 62/273,503 filed Dec. 31, 2015, the contents of which are incorporated herein by reference in their entirety.

FIELD OF INVENTION

The present invention relates to the field of intravesical therapy.

BACKGROUND

Intravesical treatment is a method that allows direct transfer of drugs into the urinary bladder (or simply 'bladder'). Standard intravesical treatment involves insertion of a urinary catheter through the urethra and into the bladder. Lumens that run along the catheter length constitute direct route in and out of the bladder, thereby allowing drainage of the bladder and irrigation with drug solutions. This site-specific treatment may have the advantage of delivering drugs directly into the bladder, as opposed to non-specific systemic treatment given orally or infused directly into the blood system. In bladder cancer treatment, for example, intravesical drug delivery may allow the delivery of cytotoxic chemotherapy drugs directly to the treatment site, thus sparing healthy tissues that would otherwise be affected under systemic treatment. Intravesical drug delivery is also used in treatments of many other ailments of the bladder, such as of cystitis, overactive bladder, and bladder infections.

Intravesical therapy may involve several challenges and limitations. The bladder inner surface is covered with transitional epithelium lining called urothelium, and glycosaminoglycans (GAG) units found on the urothelium. Both the urothelium and the GAG units may function as an important barrier to toxins and waste found in the urine, giving the bladder wall its low permeability characteristic. However, this compact and tight barrier may also restrict effective penetration of therapeutic drugs delivered into the bladder during intravesical treatments. Some therapeutic molecules may not penetrate the bladder barrier at all. For example, Botox, which is a large toxin that may be delivered to the bladder wall for the treatment of overactive bladder, may not penetrate the bladder barrier. Hence, under standard practice Botox is injected into the bladder using a cystoscope and a needle. In this procedure a cystoscope and a needle are inserted into the bladder through the urethra and the Botox is injected to the bladder detrusor at 20-30 different sites. This procedure is invasive, requires anesthesia, and involves some risks associated with needle injections. Also Botox delivery profile is not uniform—Injections of the Botox to discrete injections sites result in areas in the bladder with excess of Botox, and region in the bladder with no Botox at all.

Ultrasound cavitation is a major mechanism by which ultrasound increases tissue permeability. According to theory, cavitation bubbles collapse on the tissue with high energy and open up pores in the tissue, which results in the increased permeability of the tissue to therapeutic drugs. There may be two challenges when cavitation is concerned. The first is that cavitation may need to form in a solution in a close proximity to the tissue surface in order to increase drug delivery. The second is that cavitation bubbles may usually form near or on the ultrasonic transducer surface, thereby blocking the ultrasonic waves (see, for example: Terahara T. et al., Dependence of low-frequency sonophoresis on Ultrasound parameters; distance of the horn and intensity. *International Journal of Pharmaceutics.* 2002 Mar. 20; 235(1-2): 35-42).

Overactive bladder is a prevalent condition that has a significant impact on quality of life. The usual treatment approach is both behavioral and pharmacological. The first-line pharmacological treatment commonly utilizes anticholinergic agents, which may be limited by their tolerability, efficacy, and long-term compliance. Additional therapeutic agents include mirabegron and botulinum toxin, which may reduce the anticholinergic side effects.

The foregoing examples of the related art and limitations related therewith are intended to be illustrative and not exclusive. Other limitations of the related art will become apparent to those of skill in the art upon a reading of the specification and a study of the figures.

SUMMARY

The following embodiments and aspects thereof are described and illustrated in conjunction with systems, tools and methods which are meant to be exemplary and illustrative, not limiting in scope.

There is provided, in accordance with an embodiment, a kit comprising: a urinary catheter comprising a first and a second longitudinal lumens; at least one ultrasonic transducer disposed about a distal portion of said urinary catheter; a balloon mounted on said urinary catheter at the distal portion, and enclosing said at least one ultrasonic transducer; and a reservoir containing an acoustic coupling medium, wherein: said urinary catheter further comprises a first opening in said first longitudinal lumen, said first opening disposed inside said balloon and configured to inflate said balloon with at least some of said acoustic coupling medium, said urinary catheter further comprises a second opening in said second longitudinal lumen, said second opening disposed outside said balloon and configured to deliver a therapeutic fluid into the urinary bladder, around said balloon, and activation of said at least one ultrasonic transducer in said urinary bladder causes cavitation bubbles to form in said therapeutic fluid adjacent an internal surface of the urinary bladder, and little or no cavitation bubbles are formed in said acoustic coupling medium in said balloon.

There is provided, in accordance with another embodiment, a method for delivering a therapeutic fluid to the urinary bladder, the method comprising: inserting a distal portion of a urinary catheter and at least one ultrasonic transducer disposed thereabout into said urinary bladder, wherein said at least one ultrasonic transducer is enclosed by a balloon, inflating said balloon with an acoustic coupling medium via a first longitudinal lumen and a first opening of said urinary catheter, wherein said first opening is disposed in said first longitudinal lumen and inside said balloon, delivering to said urinary bladder, around said balloon, therapeutic fluid via a second longitudinal lumen and a second opening of said urinary catheter, wherein said second opening is disposed in said second longitudinal lumen and outside said balloon, and activating said at least one ultrasonic transducer to transmit ultrasonic waves towards an internal surface of said urinary bladder, to form cavitation bubbles in said therapeutic fluid adjacent to said internal surface and little or no cavitation bubbles in said acoustic coupling medium in said balloon.

There is provided, in accordance with a further embodiment, a device comprising: a urinary catheter comprising a first and a second longitudinal lumens; at least one ultrasonic transducer disposed about a distal portion of said urinary catheter; and a balloon mounted on said urinary catheter at the distal portion, and enclosing said at least one ultrasonic transducer; wherein: said urinary catheter further comprises a first opening in said first longitudinal lumen, said first opening disposed inside said balloon and configured to inflate said balloon with an acoustic coupling medium, said urinary catheter further comprises a second opening in said second longitudinal lumen, said second opening disposed outside said balloon and configured to deliver a therapeutic fluid into the urinary bladder, around said balloon, and activation of said at least one ultrasonic transducer in said urinary bladder causes cavitation bubbles to form in said therapeutic fluid adjacent an internal surface of the urinary bladder, and little or no cavitation bubbles are formed in said acoustic coupling medium in said balloon.

In some embodiments, the kit further comprises a reservoir containing said therapeutic fluid.

In some embodiments, the device and/or kit further comprise a cavitation monitor, wherein said cavitation monitor acquires acoustic emissions signals and transmits a digital signal. In some embodiments, the cavitation monitor comprises transducer detector disposed within said balloon. In some embodiments, the transducer detector is mounted on a distal portion of said urinary catheter.

In some embodiments, said therapeutic fluid comprises a cavitation booster selected from the group consisting of: an ultrasound contrast agent, micro-particles, nano-particles, liposomes, and a gas.

In some embodiments, said therapeutic fluid comprises one or more therapeutic agents selected from the group consisting of: a drug, a chemotherapeutic agent, a tracer, a marker, a radioactive compound, a small molecule, and a gene.

In some embodiments, said one or more therapeutic agents are selected from the group consisting of: anti muscarinic agents, anticholinergic agents, anesthetic agents, and botulinum toxins.

In some embodiments, said chemotherapeutic agent is selected from the group consisting of: Bacillus Calmette Guerin (BCG) vaccine, cisplatin, doxorubicin, valrubicin, gemcitabine, mycobacterial cell wall-DNA complex (MCC), methotrexate, vinblastine, thiotepa, mitomycin, fluorouracil, leuprolide, diethylstilbestrol, estramustine, megestrol acetate, cyproterone, flutamide, a selective estrogen receptor modulators (i.e. a SERM, such as tamoxifen), botulinum toxins, and cyclophosphamide.

In some embodiments, said at least one ultrasonic transducer is structured to produce an unfocused, diverging acoustic field.

In some embodiments, said at least one ultrasonic transducer is at least one tubular transducer surrounding a section of said urinary catheter.

In some embodiments, said at least one ultrasonic transducer is a flat, rectangular transducer.

In some embodiments, said urinary catheter further comprises a third longitudinal lumen and a third opening disposed inside said balloon, to allow circulating said at least some of said acoustic coupling medium in and out of said balloon, thereby cooling said at least some of said acoustic coupling medium.

In some embodiments, the kit further comprises a rotation unit configured to rotate at least said at least one ultrasonic transducer when said at least one ultrasonic transducer is activated.

In some embodiments, the balloon is shaped similarly to the shape of the urinary bladder and is smaller in size than the urinary bladder.

In some embodiments, the device and/or kit further comprise one or more spacers disposed on an external surface of said balloon.

In some embodiments, the device and/or kit further comprise a net surrounding said balloon.

In some embodiments, the balloon comprises a rough external surface.

In some embodiments, said at least one ultrasonic transducer is configured to resonate at a frequency between 36 Kilohertz and 550 Kilohertz.

In some embodiments, said at least one ultrasonic transducer is configured to resonate at a frequency between 36 Kilohertz and 100 Kilohertz. In some embodiments, said at least one ultrasonic transducer is configured to resonate at a frequency between 50 Kilohertz and 100 Kilohertz.

In some embodiments, said at least one ultrasonic transducer is configured to resonate at a frequency between 36 Kilohertz and one Megahertz and at a frequency above one Megahertz.

In some embodiments, said at least one ultrasonic transducer is a plurality of flat, rectangular transducers arranged around a section of said urinary catheter.

In some embodiments, said urinary catheter further comprises a third longitudinal lumen and a third opening disposed inside said balloon, and wherein said method further comprises circulating said at least some of said acoustic coupling medium in and out of said balloon via said first and third longitudinal lumens to cool said at least some of said acoustic coupling medium.

In some embodiments, the method further comprises rotating at least said at least one ultrasonic transducer when said at least one ultrasonic transducer is activated.

In some embodiments, the method further comprises rotating said urinary catheter.

In some embodiments, the method further comprises iteratively activating said at least one ultrasonic transducer and each time said urinary catheter is rotated.

In addition to the exemplary aspects and embodiments described above, further aspects and embodiments will become apparent by reference to the figures and by study of the following detailed description.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. The figures are listed below.

DETAILED DESCRIPTION

Figure 1:
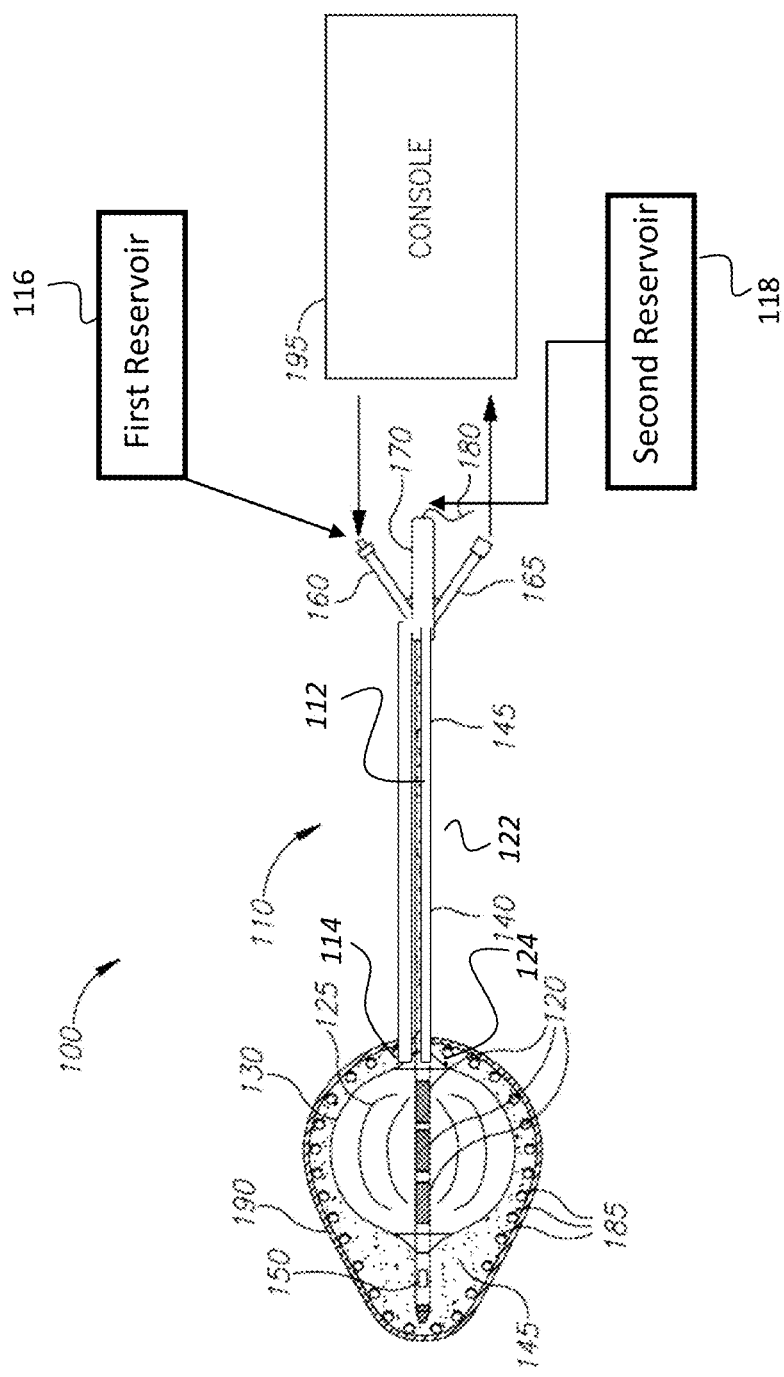
FIG. 1 shows a top view and partially transparent of an exemplary device disposed within a urinary bladder, according to an embodiment.

The disclosed device, kit and method may increase the permeability of the urinary bladder (or simply 'bladder') tissue and/or prostate tissue to therapeutic agents such as drugs. By allowing the delivery of higher drug concentration, for example, into bladder internal surface and into deeper layers of the bladder wall, improvement of standard intravesical bladder therapy may be achieved. A skilled artisan will appreciate the advantage of utilizing the device of the instant invention for drug (e.g., Botox) delivery, such as to the bladder wall, over common methods which include multiple injections of the drugs to the bladder wall. The disclosed device, kit and method are based on the application of ultrasound to the bladder tissue and/or to a therapeutic agent adjacent to the bladder internal surface. Ultrasound may increase permeability through thermal and/or cavitation mechanisms. The disclosed device, kit and method may utilize one or both mechanisms in order to improve the delivery of therapeutic agents into bladder tissue. The disclosed device, kit and method further deliver a therapeutic agent, a drug, marker, a radioactive molecule, a chemotherapeutic compound or any combination thereof. The disclosed device, kit and method further enhance and/or facilitate the in-situ delivery of a therapeutic agent, a drug, marker, a radioactive molecule, a chemotherapeutic compound or any combination thereof into a target tissue such as but not limited to the: bladder or urethra and/or prostate. The disclosed device, kit and method further enhance the permeability of a target tissue thus enhancing in-situ delivery of a therapeutic agent into the target tissue and/or a bladder.

In general, under ultrasound irradiation of the bladder, cavitation bubbles may form anywhere in the fluid contained in the bladder. Moreover, in the case that an ultrasound transducer applies ultrasound from within the bladder, cavitation bubbles may form on the transducer itself, or near the transducer's surface, often blocking ultrasound energy from reaching the bladder wall. Even at low bladder volumes, the bladder wall may be up to four centimeters distant from the center of the bladder. Hence, it may be unlikely to produce cavitation only or substantially near the internal surface of the bladder (i.e., and not near the surface of the transducer) from an ultrasound transducer radiating from a centralized position in the bladder.

The disclosed device, kit and method may allow controlling of the cavitation formation and location. Cavitation bubbles may be formed near the bladder internal surface, in order to increase the delivery of therapeutic agents. Furthermore, cavitation may be prevented or substantially prevented from forming near the ultrasonic transducer and from blocking ultrasound energy (also called a "shielding effect") from reaching bladder wall. Cavitation bubbles may be formed near the bladder internal surface without the need to mount the ultrasonic transducer (or simply 'transducer') very close to the bladder internal surface (e.g., in a distance of less than one centimeter or even in contact with the internal surface). As a result, in some embodiments of the disclosed device, kit and method, the transducer may be distant from the bladder internal surface. For example, the transducer may be mounted in a position which is distant by up to 8 centimeters (cm) from the bladder internal surface, and in some embodiments even more.

The control of cavitation formation and location may be achieved by enclosing the transducer with a balloon filled with an acoustic coupling medium which does not favor cavitation, such as a degassed solution. In such a solution, cavitation may not form or substantially may not form. Hence, the one or more transducers (which may be disposed, for example, on a urinary catheter and inside the balloon) may be immersed in an acoustic coupling medium, and cavitation may not form on or near the transducers. Thus, cavitation may not block ultrasound energy directed to bladder.

In order to form cavitation near the bladder internal surface, cavitation may be formed in a therapeutic fluid that interacts with the bladder. In one non-limiting example, the therapeutic fluid may include the therapeutic agent to be delivered to the bladder and is introduced to the cavity between the balloon and the bladder internal surface. In yet another example, the therapeutic agent may be introduced to the therapeutic fluid following the application of ultrasonic radiation (e.g., 1-2 hours following the operation of the ultrasound transducers).

This therapeutic fluid may allow the formation of cavitation under ultrasound which may increase bladder permeability. Optionally, the ultrasound waves pushes the therapeutic agent into the bladder wall. In order to encourage cavitation in the therapeutic fluid, its gas content may be increased. Alternatively, cavitation boosters (i.e., a cavitation favoring agents) may be added to the therapeutic fluid. Non-limiting examples of cavitation boosters include ultrasound contrast agents, such as microbubbles (e.g., Definity®, Optison® and SonoVue®), micro-particles, nano-particles, or liposomes. In this manner, the intensity levels needed to form cavitation may be decreased. In some embodiments, the therapeutic agents may be encapsulated in the cavitation boosters, which may results in a more efficient delivery of the therapeutic agent to the bladder wall.

Optionally, when the ultrasound transducers are external ultrasound transducers, the balloon may be filled with gas (e.g., air, argon, etc.) and the cavity between the balloon and the bladder internal surface may be filled with a therapeutic fluid with decreased cavitation threshold (e.g., supplemented with microbubbles, micro-particles, nano-particles, and/or liposomes). Thus, when the external ultrasound transducers are utilized, acoustic energy reflects and bends around a surface of the balloon, rather than penetrate the balloon. When the external ultrasound transducers are utilized, acoustic pressure may increase in the therapeutic fluid and at some level of acoustic pressure the cavitation in the layer between the balloon surface and the bladder surface will be initiated.

In some embodiments, the balloon is filled with a fluid. Optionally, the balloon comprises an aqueous solution. Optionally, the balloon comprises a gel or a viscous liquid. Optionally, the viscous liquid has a viscosity of at least 1.0020 mPa·s at 20° C. Optionally, the viscous liquid has a viscosity of at least 1.1 mPa·s, 1.2 mPa·s, 1.3 mPa·s, 1.4 mPa·s, 1.5 mPa·s, 1.6 mPa·s, 1.7 mPa·s, 1.8 mPa·s, 1.9 mPa·s, 2 mPa·s, 2.2 mPa·s, 2.4 mPa·s, 2.6 mPa·s, 3 mPa·s, or 3.5 mPa·s. Optionally, viscosity is dynamic viscosity.

The balloon may be made of a wide variety of materials including, for example, polytetrafluoroethylenes (Teflon®), polyethylenes, (e.g., high density polyethylenes), polyethylene terephthalate (PET), polypropylenes, polyurethanes, nylons including nylon 6 and nylon 12, polyesters including polyalkylene terephthalate polymers and copolymers, (e.g., thermoplastic polyester elastomers such as Hytrel®, which is a block copolymer containing a hard polybutylene terephthalate segment and soft amorphous segments based on long-chain polyether glycols), polyimides, polyamides including polyether-block-co-polyamide polymers (e.g., Pebax®), and the like. These materials may also be blended or provided in a composite or multi-layer construction. Typically, PET balloons are substantially optically clear and permit the transmission of light over a broad spectrum.

Optionally, an outer surface of the balloon which interacts with the therapeutic fluid may be configured to trap cavitation nuclei (seeds) and increase cavitation phenomenon in the therapeutic fluid (e.g., a rough outer surface). As used herein, the term "rough outer surface" refers to a surface having multi-faceted symmetrical or non-symmetrical features containing points, ridges and multifaceted edges and angles. A roughness value may be calculated on a profile (line). For example, Ra is the arithmetic average of the absolute values of the profile height deviations from the mean line, and its value is expressed in micrometers (μm). Optionally, the "rough outer surface" may have an Ra value of 10 to 100 μm, 100 to 200 μm, 200 to 300 μm, 300 to 400 μm, 400 to 500 μm, 500 to 600 μm, 600 to 700 μm, 700 to 800 μm, 800 to 900 μm, or 900 to 1000 μm. Alternatively, the balloon may be covered with a net or a mesh which traps cavitation seeds and encourages cavitation.

In addition, the disclosed device, kit and method may allow pushing molecules of a therapeutic agent towards the bladder internal surface. In standard practice, the bladder may be filled with therapeutic fluid, and the molecules of the therapeutic fluid (i.e., including the molecules of the therapeutic agent, if included or when added) float in the fluid found in the entire bladder space. Thus, only a small fraction of the total number of the therapeutic agent molecules may come in contact with the bladder lining. Ultrasound cavitation phenomenon near bladder internal surface, such as streaming and micro-steaming, may push the therapeutic agent into the bladder internal surface. Hence, forming cavitation near the bladder wall may effectively increase the fraction of therapeutic agent molecules that interact with the bladder lining.

The term "cavitation", as referred to herein, may relate to the formation and collapse of cavities (bubbles) in a liquid which undergoes a rapid pressure fluctuation generated by an acoustic source (e.g., ultrasound). Reference is often made to two types of ultrasound induced cavitation, referred to as inertial and stable cavitation. Inertial cavitation is characterized by bubbles which grow and implode violently within a few cycles of excitation, collapsing bubbles produce shock waves characterized by wide-band acoustic spectra, up to 15-20 Megahertz (MHz). During cavitation event, many bubbles implode thus a resulting acoustic signal would be observed as a random noise having a wide spectrum up to 20 MHz or even wider. Stable cavitation is characterized by bubbles which sustain and repetitively oscillate for a longer period of time. The acoustic emission is characterized by harmonics and sub-harmonics of the operational frequency ($f_0$) of the High-Intensity Ultrasound Transducer ("HIUT"). The most prominent ones are $f_0/2$, $2f_0$, $3f_0$, $3f_0/2$ and $5f_0/2$, the last two are called ultraharmonics. All these signals may be monitored by an acousto-electric sensor, which converts acoustic pressure into electric signals. The most common type of such sensor is a piezoelectric transducer. Methods for cavitation monitoring are well known in the art, a main quantitative technique for cavitation detection and measurement is passive cavitation detection, which exploits the acoustic emissions generated by cavitating bubbles. Passive techniques use ultrasound transducers, which may have different shapes, usually focused or planar, called a Passive Cavitation Detector (PCD), to acquire acoustic emissions signals resulting from cavitation. Passive cavitation detection can be easily implemented and has been widely used over a range of applications.

The term "therapeutic agent", as referred to herein, may relate to any therapeutic substance, such as a drug (e.g., Botox), a chemotherapeutic agent, a tracer, a marker, a radioactive compound, a small molecule, or a gene.

The term "therapeutic fluid", as referred to herein, may relate to a fluid, which includes a therapeutic agent or designated to be added with the therapeutic agent following the application of ultrasonic radiation. The therapeutic fluid may be, for example, a solution, where the solute is the therapeutic agent and the solvent may be, for example, saline, ethanol, water or acetic acid. Accordingly, in some embodiments, the therapeutic fluid may at first include only the solvent, and later it may be added with the therapeutic agent. In some embodiments, a "therapeutic fluid" comprises a probing agent which binds, adheres or marks/identifies a specific tissue or a cell type such as but not limited to a cancerous cell. In some embodiments, a probing agent is a labeled compound. In some embodiments, a probing agent is a radioactive compound. In some embodiments, a probing agent is a labeled compound. In some embodiments, a probing agent is fluorescently labeled.

The terms "tissue" and "wall", as referred to herein with respect to a urinary bladder, may relate to the tissue forming the urinary bladder, and may be used interchangeably. The term "internal surface", as referred to herein with respect to the urinary bladder, may relate to the internal surface of such wall or tissue of the bladder. These terms may relate to the entire and/or to a portion of the bladder, according to their context.

The term "acoustic coupling medium", as referred to herein, may relate to a medium which allows efficient progression of ultrasound energy. An important aspect of this medium is that it does not favor cavitation phenomenon, which may block ultrasound energy from progressing from the transducer to the bladder internal surface. Such medium may be degassed (i.e., its gases were removed), e.g., degassed solution such as saline which went through boiling, or a solution which its gas content was filtered out.

The chemotherapeutic agent is, in some embodiments, a bladder chemotherapeutic agent. The drug, in some embodiments, is an intra-bladder medicament. The therapeutic agent is, in some embodiments, botulinum toxin or onabotulinumtoxinA (also known as Botox). The therapeutic agent is, in some embodiments, an overactive bladder medicament. The therapeutic agent is, in some embodiments, an anti-muscarinic agent, an anticholinergic agent or a combination thereof. The therapeutic agent is, in some embodiments, an anesthetic agent. In some embodiments, overactive bladder includes urinary urgency, frequency and nocturia, and incontinence.

In some embodiments, the therapeutic agent or drug is any therapeutic, prophylactic, or diagnostic agent, such as one that would be useful to release locally into the prostate, bladder, or ureter for local or regionally treatments. The kit, methods and device of the invention enhance and/or facilitate the in-situ delivery of the therapeutic agent compared to traditional delivery methods such as site specific injection or systemic delivery. Delivery may be in a faster and/or more uniform manner. Optionally, higher concentration of the therapeutic drugs may be delivered compared to traditional delivery methods. Optionally, delivery to deeper layer of the bladder wall may be facilitated, compared to traditional delivery methods. The kit, methods and device of the invention enhance and/or facilitate the in-situ delivery of the therapeutic agent into the bladder or the urethra, compared to traditional delivery methods such as site specific injection or systemic delivery. The kit, methods and device of the invention, in some embodiments, reduce side effects resulting from the compounds and the traditional delivery methods such as site specific injection or systemic delivery. In some embodiments, the "therapeutic agent" or "drug" comprises one or more pharmaceutically acceptable excipients. The drug may be a biologic. The drug may be a metabolite. As used herein, the term "drug" with reference to any specific drug described herein includes its alternative forms, such as salt forms, free acid forms, free base forms, solvates, and hydrates. Pharmaceutically acceptable excipients are known in the art and may include lubricants, viscosity modifiers, surface active agents, osmotic agents, diluents, and other non-active ingredients of the formulation intended to facilitate handling, stability, dispersibility, wettability, and/or release kinetics of the drug.

The kit, methods and device of the invention is used, according to some embodiments, for treating pain. In some embodiments, the therapeutic agent or drug is an analgesic agent. In some embodiments, the therapeutic agent or drug is a cocaine analogue. In some embodiments, the therapeutic agent or drug is an aminoamide. In some embodiments, the therapeutic agent or drug is an aminoesteror ester-class anesthetic. In some embodiments, the therapeutic agent or drug is lontocaine. In some embodiments, the therapeutic agent or drug is oxybutynin or propiverine.

In some embodiments, the therapeutic agent or drug is an opioid or an opioid agonist such as but not limited to: alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, proheptazine, promedol, properidine, propiram, propoxyphene, sufentanil, tilidine, tramadol, pharmaceutically acceptable salts thereof, and mixtures thereof. In some embodiments, the therapeutic agent or drug is a mu, kappa, delta, or nociception opioid receptor agonists.

In some embodiments, the therapeutic agent or drug is an analgesic such as but not limited to: acetaminophen, buprenorphine, butorphanol, codeine, dihydrocodeine, fentanyl, heroin, hydrocodone, hydromorphone, methadone, morphine, nicomorphine, oxycodone, oxymorphone, pentazocine, pethidine, propoxyphene, pyridium (phenazopyridine), thebaine, tramadol, alicyl alcohol, phenazopyridine hydrochloride, acetylsalicylic acid, flufenisal, ibuprofen, indoprofen, indomethacin, naproxen, or any combination thereof.

In some embodiments, the device, kit and methods are utilized for treating an inflammatory condition or inflammation. In some embodiments, the device, kit and methods are utilized for treating radiation cystitis, prostatitis, urethritis, post-surgical pain, or kidney stones. In some embodiments, the therapeutic agent or drug is: lidocaine, glycosaminoglycans (e.g., chondroitin sulfate, sulodexide), pentosan polysulfate sodium (PPS), dimethyl sulfoxide (DMSO), oxybutynin, mitomycin C, heparin, flavoxate, ketorolac, or a combination thereof. In some embodiments, the therapeutic agent or drug is Tanezumab or a channel alpha-2-delta modulator (such as PD-299685 or gabapentin).

In some embodiments, the device, kit and methods are utilized for the placement of a ureteral stent, such as to treat pain, urinary urgency or urinary frequency resulting from ureteral stent placement. Non-limiting examples of specific drugs for such treatment include anti-muscarinics, a-blockers, narcotics, and phenazopyridine, among others.

In some embodiments, the device, kit and methods are utilized for treating urinary incontinence, frequency, or urgency, including urge incontinence and neurogenic incontinence, as well as trigonitis. Drugs that may be used include anticholinergic agents, antispasmodic agents, anti-muscarinic agents, β-2 agonists, alpha adrenergics, anticonvulsants, norepinephrine uptake inhibitors, serotonin uptake inhibitors, calcium channel blockers, potassium channel openers, and muscle relaxants. Representative examples of suitable drugs for the treatment of incontinence include oxybutynin, S-oxybutytin, emepronium, verapamil, imipramine, flavoxate, atropine, propantheline, tolterodine, rociverine, clenbuterol, darifenacin, terodiline, trospium, hyoscyamin, propiverine, desmopressin, vamicamide, clidinium bromide, dicyclomine HCl, glycopyrrolate aminoalcohol ester, ipratropium bromide, mepenzolate bromide, methscopolamine bromide, scopolamine hydrobromide, iotropium bromide, fesoterodine fumarate, YM-46303 (Yamanouchi Co., Japan), lanperisone (Nippon Kayaku Co., Japan), inaperisone, NS-21 (Nippon Shinyaku Orion, Formenti, Japan/Italy), NC-1800 (Nippon Chemiphar Co., Japan), Z D-6169 (Zeneca Co., United Kingdom), and stilonium iodide.

In some embodiments, the device, kit and methods are utilized for treating urinary tract cancer, such as bladder cancer and prostate cancer. Drugs that may be used include antiproliferative agents, cytotoxic agents, chemotherapeutic agents, or a combination thereof. Representative examples of drugs which may be suitable for the treatment of urinary tract cancer include Bacillus Calmette Guerin (BCG) vaccine, cisplatin, doxorubicin, valrubicin, gemcitabine, mycobacterial cell wall-DNA complex (MCC), methotrexate, vinblastine, thiotepa, mitomycin, fluorouracil, leuprolide, diethylstilbestrol, estramustine, megestrol acetate, cyproterone, flutamide, a selective estrogen receptor modulators (i.e. a SERM, such as tamoxifen), botulinum toxins, and cyclophosphamide. The drug may be a biologic, and it may comprise a monoclonal antibody, a TNF inhibitor, an anti-leukin, or the like. The drug also may be an immunomodulator, such as a TLR agonist, including imiquimod or another TLR7 agonist. The drug also may be a kinase inhibitor, such as a fibroblast growth factor receptor-3 (FGFR3)-selective tyrosine kinase inhibitor, a phosphatidylinositol 3 kinase (PI3K) inhibitor, or a mitogen-activated protein kinase (MAPK) inhibitor, among others or combinations thereof. Other examples include celecoxib, erolotinib, gefitinib, paclitaxel, polyphenon E, valrubicin, neocarzinostatin, apaziquone, Belinostat, Ingenol mebutate, Urocidin (MCC), Proxinium (VB 4845), BC 819 (BioCancell Therapeutics), Keyhole limpet haemocyanin, LOR 2040 (Lorus Therapeutics), urocanic acid, OGX 427 (OncoGenex), and SCH 721015 (Schering-Plough). Other intravesical cancer treatments include small molecules, such as Apaziquone, adriamycin, AD-32, doxorubicin, doxetaxel, epirubicin, gemcitabine, HTI-286 (hemiasterlin analogue), idarubicin, γ-linolenic acid, mitozantrone, meglumine, and thiotepa; large molecules, such as Activated macrophages, activated T cells, EGF-dextran, HPC-doxorubicin, IL-12, IFN-a2b, IFN-γ, a-lactalbumin, p53 adenovector, TNFa; combinations, such as Epirubicin+BCG, IFN+farmarubicin, Doxorubicin+5-FU (oral), BCG+IFN, and Pertussis toxin+cystectomy; activated cells, such as macrophages and T cells; intravesical infusions such as IL-2 and Doxorubicin; chemosensitizers, such as BCG+antifirinolytics (paramethylbenzoic acid or aminocaproic acid) and Doxorubicin+verapimil; diagnostic/imaging agents, such as Hexylaminolevulinate, 5-aminolevulinic acid, Iododexyuridine, HMFG1 Mab+Tc99m; and agents for the management of local toxicity, such as Formaline (hemorrhagic cystitis).

In some embodiments, the device, kit and methods are utilized for treating infections involving the bladder, the prostate, and the urethra. In some embodiments, the drug is an antibiotics, an antibacterial, an antifungal, an antiprotozoal, an antiseptic, an antiviral or any other anti-infective agent.

In some embodiments, the therapeutic agent or drug is mitomycin, ciprofloxacin, norfloxacin, ofloxacin, methanamine, nitrofurantoin, ampicillin, amoxicillin, nafcillin, trimethoprim, sulfonamides trimethoprimsulfamethoxazole, erythromycin, doxycycline, metronidazole, tetracycline, kanamycin, penicillins, cephalosporins, or an aminoglycoside.

In some embodiments, the device, kit and methods are utilized for treating fibrosis of a genitourinary site, such as but not limited to the bladder or uterus. In some embodiments, the device, kit and methods are utilized for treating a neurogenic bladder. In some embodiments, the therapeutic agent or drug is pentoxphylline (xanthine analogue), an anti-TNF-αgent, an anti-TGF agents, a GnRH analogue, an exogenous progestin, an antiprogestins, a selective estrogen receptor modulator, danazol, a NSAID, or any combination thereof. In some embodiments, the therapeutic agent or drug is a known drug for the treatment of incontinence due to neurologic detrusor overactivity and/or low compliant detrusor. Examples of these types of drugs include bladder relaxant drugs (e.g., oxybutynin (antimuscarinic agent with a pronounced muscle relaxant activity and local anesthetic activity), propiverine, impratroprium, tiotropium, trospium, terodiline, tolterodine, propantheline, oxyphencyclimine, flavoxate, and tricyclic antidepressants; drugs for blocking nerves innervating the bladder and urethra (e.g., vanilloids (capsaicin, resiniferatoxin), botulinum-A toxin); or drugs that modulate detrusor contraction strength, micturition reflex, detrusor sphincter dyssynergia (e.g., GABAb agonists (baclofen), benzodiazapines). In another embodiment, the drug is selected from those known for the treatment of incontinence due to neurologic sphincter deficiency. Examples of these drugs include alpha adrenergic agonists, estrogens, beta-adrenergic agonists, tricyclic antidepressants (imipramine, amitriptyline). In still another embodiment, the drug is selected from those known for facilitating bladder emptying (e.g., alpha adrenergic antagonists (phentolamine) or cholinergics). In yet another embodiment, the drug is selected from among anticholinergic drugs (e.g., dicyclomine), calcium channel blockers (e.g., verapamil) tropane alkaloids (e.g., atropine, scopolamine), nociceptin/orphanin FQ, and bethanechol (e.g., m3 muscarinic agonist, choline ester).

In some embodiments, the therapeutic agent or drug is oxybutynin. In some embodiments, the therapeutic agent or drug is a β-3 adrenergic receptor (β3-AR) agonist. In another embodiment, the therapeutic agent or drug is oxybutynin. In another embodiment, the therapeutic agent or drug is Tolterodine tartrate. In another embodiment, the therapeutic agent or drug is Fesoterodine fumarate. In another embodiment, the therapeutic agent or drug is Solifenacin. In another embodiment, the therapeutic agent or drug is Trospium chloride. In another embodiment, the therapeutic agent or drug is Darifenacin. In another embodiment, the therapeutic agent or drug is Propiverine. In another embodiment, the therapeutic agent or drug is a Tricyclic antidepressant. In another embodiment, the therapeutic agent or drug is Desmopressin. In another embodiment, the therapeutic agent or drug is an estrogen therapeutic agent.

In some embodiments, a drug or an agent as described herein is within a "therapeutic fluid". In some embodiments, a "therapeutic fluid" is a pharmaceutical composition. In some embodiments, a "therapeutic fluid" is a liquid pharmaceutical composition. In some embodiments, a "therapeutic fluid" is an aqueous pharmaceutical composition.

In some embodiments, the present invention provides a superior in vivo delivery system for a compound to be delivered into a bladder tissue. In some embodiments, the present invention provides an enhanced dispersion of a compound to be delivered into a bladder tissue. In some embodiments, the present invention provides enhanced and deeper tissue penetration of a compound to be delivered into a bladder tissue. In some embodiments, the present invention provides a faster in vivo delivery system that is capable of delivering to a compound to be delivered into a bladder tissue. In some embodiments, the kit and/or system as described herein increases and/or enhances the area under the curve (AUC) measure of a compound present within the therapeutic fluid. In some embodiments, the kit and/or system as described herein reduces the halftime ($t^{1/2}$) measure of a compound present within the therapeutic fluid. In some embodiments, the kit and/or system as described herein increases and/or enhances the Cmax measure of a compound present within the therapeutic fluid. In some embodiments, the kit and/or system as described herein increases and/or enhances the Vmax measure of a compound present within the therapeutic fluid.

In some embodiments, the present invention reduces the risk of (a) long-term increase in tissue permeability and/or (b) long-term decrease tissue integrity within a bladder, due to the delivery of a therapeutic fluid with the systems and kits as described herein. In some embodiments, the risk of increase in tissue permeability and decrease in tissue integrity is apparent days, weeks or months after a procedure such as described herein, is performed. In some embodiments, the present invention provides efficient means (the kits and systems) for penetration and delivery of a therapeutic agent into a bladder without causing prolonged and/or terminal damage to the bladder tissue. In some embodiments, the present invention provides efficient means (the kits and systems) for reducing nonspecific delivery of a therapeutic agent into a bladder tissue.

In some embodiments, the present invention provides that at least 30% of the therapeutic compound/drug or therapeutic fluid within the system and/or kit, penetrates and/or being absorbed within a bladder tissue. In some embodiments, the present invention provides that at least 40% of the therapeutic compound/drug or therapeutic fluid within the system and/or kit, penetrates and/or being absorbed within a bladder tissue. In some embodiments, the present invention provides that at least 50% of the therapeutic compound/drug or therapeutic fluid within the system and/or kit, penetrates and/or being absorbed within a bladder tissue. In some embodiments, the present invention provides that at least 60% of the therapeutic compound/drug or therapeutic fluid within the system and/or kit, penetrates and/or being absorbed within a bladder tissue. In some embodiments, the present invention provides that at least 70% of the therapeutic compound/drug or therapeutic fluid within the system and/or kit, penetrates and/or being absorbed within a bladder tissue. In some embodiments, the present invention provides that at least 80% of the therapeutic compound/drug or therapeutic fluid within the system and/or kit, penetrates and/or being absorbed within a bladder tissue. In some embodiments, the present invention provides that at least 85% of the therapeutic compound/drug or therapeutic fluid within the system and/or kit, penetrates and/or being absorbed within a bladder tissue. In some embodiments, the present invention provides that at least 90% of the therapeutic compound/drug or therapeutic fluid within the system and/or kit, penetrates and/or being absorbed within a bladder tissue.

In some embodiments, the present invention provides efficient means (the kits and systems) for local delivery of drugs directly into the bladder. In some embodiments, the present invention provides kits and systems which minimize systemic bioavailability of the delivered therapeutic agent or drug. In some embodiments, the present invention provides kits and systems ensuring minimal adverse toxicity.

In one embodiment, a device, kit and/or system as described herein continuously releases the therapeutic fluid. In one embodiment, a device, kit and/or system as described herein releases the therapeutic fluid into the urine in the bladder over a sustained period. In one embodiment, a device, kit and/or system as described herein releases fixed dosages of the therapeutic fluid in pulses over a sustained period. In one embodiment, a device, kit and/or system as described herein comprises a predefined release aperture. In one embodiment, a device, kit and/or system as described herein comprises a therapeutic fluid reservoir portion or chamber.

In one embodiment, a device, kit and/or system as described herein provides that the therapeutic agent is maintained within the target tissue/bladder for at least 1 hour. In one embodiment, a device, kit and/or system as described herein provides that the therapeutic agent is maintained within the target tissue/bladder for at least 2 hours. In one embodiment, a device, kit and/or system as described herein provides that the therapeutic agent is maintained within the target tissue/bladder for at least 2.5 hours. In one embodiment, a device, kit and/or system as described herein enables the retention of the therapeutic agent within the target tissue/bladder for at least 3 hours. In one embodiment, a device, kit and/or system as described herein provides prolonged exposure of the therapeutic agent/drug within the urothelium. In one embodiment, a device, kit and/or system as described herein enables the exposure of the therapeutic agent/drug within the urothelium beyond the first, second, and/or third voiding of urine In some embodiments, a "therapeutic fluid" comprises liquid solutions, emulsions, suspensions, and the like. In some embodiments, pharmaceutically-acceptable carriers suitable for preparation of such compositions (therapeutic fluid) are well known in the art. In some embodiments, therapeutic fluid comprises from about 0.012% to about 0.933% of the desired compound drug or compounds/drugs, or in another embodiment, from about 0.033% to about 0.7%.

In some embodiments, therapeutic fluid for use in the methods, kits and devices of this invention comprise solutions or emulsions, which in some embodiments are aqueous solutions or emulsions comprising a safe and effective amount of the compounds of the present invention and optionally, other compounds. In some embodiments, the compositions comprise from about 0.01% to about 10.0% w/v of a subject compound or from about 0.1% to about 2.0.

In some embodiments, therapeutic fluid includes solutions, suspensions, dispersions, emulsions, oils and the like with or without a pharmaceutical carrier. In one embodiment, therapeutic fluid includes a compatible buffer such as Hank's solution, Ringer's solution, or physiological salt buffer. In some embodiments, therapeutic fluid includes a penetrant.

In some embodiments, the therapeutic fluid is in unit dosage form, e.g., in ampoules or in multidose containers with optionally, an added preservative. In some embodiments, the therapeutic fluid is a suspension, solution or emulsion in oily or aqueous vehicle, and comprise a formulatory agent such as suspending, stabilizing and/or dispersing agents.

In some embodiments, the therapeutic fluid comprises lipophilic solvents or vehicles such as but not limited to: fatty oils such as sesame oil, or synthetic fatty acid esters such as ethyl oleate, triglycerides or liposomes. In some embodiments, the therapeutic fluid comprises substances, which increase the viscosity of the suspension, such as sodium carboxymethyl cellulose, sorbitol or dextran. In some embodiments, the therapeutic fluid comprises suitable stabilizers or agents which increase the solubility of the active ingredients (drug and/or agent) to allow for the preparation of highly concentrated solutions.

In some embodiments, the active ingredient or drug is in powder form for constitution with a suitable vehicle, e.g., sterile, pyrogen-free water based solution, before use. In some embodiments, the phrase "detrusor overactivity" is synonymous with the phrase "overactive bladder". In some embodiments, overactive bladder is idiopathic and/or neurogenic overactive bladder. In some embodiments, overactive bladder is a pediatric overactive bladder. The therapeutic agent is, in some embodiment, a blocker of post-synaptic muscarinic receptors on the detrusor muscle. In one embodiment, the therapeutic agent is mirabegron.

Reference is now made to FIG. 1, which shows a top view and partially transparent of an exemplary device 100 disposed within a urinary bladder 190 according to an embodiment. Device 100 may be configured such that it may be introduced into urinary bladder 190 (or simply 'bladder 190'). Device 100 may include a urinary catheter 110 (or simply 'catheter 110'), ultrasonic transducers 120 and a balloon 130. Urinary catheter 110 may include a first longitudinal lumen, shown schematically at 112, a second longitudinal lumen 140, a first opening 114 and a second opening 150. Device 100 may further include electrical wires 180. Device 100 may be operatively coupled with a console 195 via electrical wires 180. Console 195 may include a power source and a pump (not shown). Electrical wires 180 may operatively couple transducers 120 with the power supply of console 195.

Please substitute the following amended paragraph for paragraph

Catheter 110 may include a distal portion and a proximal portion with respect to an operator of catheter 110 (e.g., a physician). At least the distal portion may be configured to be inserted into bladder 190. At least an end section of the proximal portion may be left outside of a patient's body and may be operatively coupled with console 195. The first longitudinal lumen 112 may extend from the end section of the proximal portion to the distal portion of catheter 110 and may be configured to receive an acoustic coupling medium maintained in a first reservoir, shown schematically at 116. The first opening 114 may be disposed in the first longitudinal lumen 112 in the distal portion of catheter 110. The first opening 112 may be disposed inside balloon 130. The first opening may be configured to inflate balloon 130 with at least some of the acoustic coupling medium. Second longitudinal lumen 140 may extend from the end section of the proximal portion to the distal portion of catheter 110 and may be configured to receive a therapeutic fluid maintained in a second reservoir, shown schematically at 118, which may include a therapeutic agent 145 (shown as molecules).

Second opening 150 may be disposed in second longitudinal lumen 140 in the distal portion of catheter 110. Second opening 150 may be disposed outside of balloon 130. Second opening 150 may be configured to deliver the therapeutic fluid (i.e., therapeutic agent 145) into bladder 190, around balloon 130.

Please substitute the following amended paragraph for paragraph

Urinary catheter 110 may include a main channel 170. Catheter 110 may further include an inlet channel 160 and an outlet channel 165. One of inlet channels 160 or 165 may be the first longitudinal lumen 112 and may include the first opening 114 while the other may be a third longitudinal lumen 122 and may include a third opening 124 disposed inside balloon 130. Inlet channel 160 may be configured to introduce the acoustic coupling medium to balloon 130. Outlet channel 165 may be configured to evacuate the acoustic coupling medium from balloon 130. Main channel 170 may include several separate channels (not shown). Main channel 170 may include a drug irrigation channel, which may be second longitudinal lumen 140. Main channel 170 may further include a channel along which electrical wires 180 may run (not shown). Electrical wires may operatively couple ultrasonic transducers 120 with the power supply of console 195.

In some embodiments, urinary catheter 110 may include three channels. In some embodiments, urinary catheter 110 may include a first main channel configured to drain the bladder and deliver drug to it; a second channel configured to allow passage of the electrical wires; and a third channel configured to allow inflation and deflation of the balloon. In some embodiments, urinary catheter 110 may include a first main channel configured to drain the bladder and deliver drug to it and to allow passage of the electrical wires; a second and a third channel configured to allow circulation of a cooled acoustic coupling medium through the balloon. In some embodiments, urinary catheter 110 may include a first and a second channel configured to circulate therapeutic fluid in the bladder; and a third channel configured to inflate and deflate the balloon. In some embodiments, urinary catheter 110 may include four channels. Such embodiments may include the three channels of the three channel embodiments, as described above, and a forth channel configured and dedicated to allow passage of the electrical wires.

In some embodiment catheter 110 may be a known catheter such as a standard Foley catheter. Alternatively, the diameter and length of catheter 110 may be similar to those of a standard Foley catheter. Optionally, the length of catheter 110 may range from 5 to 50 millimeters. In some embodiments, the diameter of catheter 110 may vary along its length, in order to accommodate the mounting of ultrasonic transducers 120.

Following the insertion of catheter 110 into bladder 190, a tip of the distal portion of catheter 110 may bend downwards due to gravity. In order to achieve a uniform Ultrasound coverage of the inner surface of bladder 190, centralization of the distal portion of catheter 110 (specifically where transducers 120 are disposed) in bladder 190 may be of importance. Thus, in some embodiments, catheter 110 may be stiff, which may allow some resistance to the pull of gravity. In some other embodiments, the distal portion of catheter 110 may include a stiffening tube inserted therewithin (e.g., in a distal portion of main channel 170) for centralizing the distal portion of catheter 110 in bladder 190 when catheter 110 is positioned therewithin.

Transducers 120 may be configured to produce ultrasonic waves. Device 100 may include at least one transducer 120.

In the exemplary embodiment of FIG. 1, device 100 includes three transducers 120. In some embodiments, device 100 may include between 5 to 15 transducers 120.

Transducers 120 may be configured to resonate at a frequency between 36 Kilohertz and 1 Megahertz. Optionally, transducers 120 may be configured to resonate at a frequency between 550 Kilohertz and 1 Megahertz. Alternatively, transducers 120 may be configured to resonate at a frequency between 36 Kilohertz and 550 Kilohertz. In addition, transducers 120 may be also configured to resonate at a frequency above one Megahertz. In some embodiments, transducers 120 may be configured to resonate at a frequency of 1 Megahertz. In some embodiments, transducers 120 may be configured to resonate at a frequency between 40 Kilohertz and 100 Kilohertz. In some embodiments, transducers 120 may be configured to resonate at a frequency between 40 Kilohertz and 300 Kilohertz. In some embodiments, transducers 120 may be configured to resonate at a frequency between 300 Kilohertz and 550 Kilohertz. In some embodiments, transducers 120 may be configured to resonate at a frequency between 400 Kilohertz and 550 Kilohertz. In some embodiments, transducers 120 may be configured to resonate at a frequency between 40 Kilohertz and 150 Kilohertz. In some embodiments, transducers 120 may be configured to resonate at a frequency between 50 Kilohertz and 200 Kilohertz. In some embodiments, transducers 120 may be configured to resonate at a frequency between 150 Kilohertz and 200 Kilohertz. In some embodiments, transducers 120 may be configured to resonate at a frequency between 170 Kilohertz and 190 Kilohertz. In some embodiments, transducers 120 may be configured to resonate at a frequency about 180 Kilohertz. In some embodiments, transducers 120 may resonate at one of the frequencies ranges listed above and may be additionally configured to resonate at a frequency above 1 Megahertz. In some embodiments, transducers 120 may be additionally configured to resonate at a frequency between 1 and 5 Megahertz. Such transducers may be used to improve the delivery of a therapeutic agent through the non-thermal cavitation mechanism, which is usually attributed to low frequencies, and the thermal mechanism, which is usually attributed to high frequencies, resulting in hyperthermia of the bladder tissue. Such hyperthermia of the bladder may have therapeutic effects solely due to the heating of the bladder wall. The synergistic thermal and cavitational effects may improve the therapeutic treatment of the bladder.

In some embodiments, in which cavitation boosters are delivered to the medium between the balloon and the bladder internal surface, transducers 120 may be configured to resonate at a frequency above one Megahertz. Such frequency level may achieve both cavitation and hyperthermia due to the addition of the cavitation boosters. Thus, a synergistic effect may be achieved by causing a synchronous cavitation of the cavitation boosters and heating of the bladder. This may improve the therapeutic treatment of the bladder. In some embodiment, usage of the cavitation boosters may be made while operating transducers 120 at a frequency below one Megahertz.

Ultrasound energy may desirably irradiate the entire internal surface of bladder 190 in order to achieve a uniform transfer of therapeutic agent 145 to bladder 190 (i.e., entirely). In order to achieve that, different configurations and shapes of transducers 120 may be utilized.

Transducers 120 may be disposed about the distal portion of catheter 110. For example, one or more of transducers 120 may be disposed on an outer surface of the distal portion of catheter 110 or one or more of transducers 120 may be disposed within the distal portion of catheter 110. Transducers 120 may be disposed in the distal portion of catheter 110 with gaps therebetween. Transducers 120 may be disposed within balloon 130, as shown in FIG. 1.

Transducers 120 may be shaped in various forms, such as radial forms, e.g., a tube (i.e., tubular transducers), or flat forms, e.g., a flat rectangular or a disc. Transducers 120 of different shapes may be mounted on or disposed within catheter 110.

In some embodiments, transducers 120 may be covered with a layer made of, e.g., silicone, polyurethane, epoxy, and parylene, in order to protect transducers 120, attach them to catheter 110, and/or allow their easy passage through the urethra. The layer thickness may be between 0.009 mm to 0.7 mm. In some embodiments, in which transducers 120 are mounted on a standard silicone Foley catheter, a continuous cover, made, for example, of silicone, may be applied covering the catheter and ultrasound transducers 120. A cover made of silicone material may be used which may allow the silicone glue to adhere strongly to the silicone catheter. In addition, the silicone cover may be relatively elastic, thus allowing for an easier and safer passage of transducers 120 through the urethra. Lastly, the silicone cover may protect transducers 120 from damage which may be caused by cavitation.

Transducers 120 may be piezo elements (i.e., piezoelectric transducers). In some embodiments, transducers 120 may be structured to produce a non-focused diverging acoustic field, for example, by using tubular piezo elements. Tubular transducers may surround a section of the catheter. With reference to FIG. 1, one configuration of such tubular piezo elements is shown. Thus, transducers 120 surround a section of the distal portion of catheter 110. Thus, transducers 120 may radiate ultrasonic waves 125 outwards in the radial direction, thereby allowing treating of at least the entire internal surface of bladder 190 synchronously. In such configuration, at least one piezo tube (i.e., transducer 120) may be used to treat bladder 190. In order to maintain catheter flexibility, a multiplicity of piezo tube elements which may have gaps separating between them may be used.

The length of a tubular transducer may range between 0.9 millimeter (mm) and 30 mm. In some embodiments, the length of each tubular transducer may be between 1 to 50 mm. In some embodiments, the length of each tubular transducer may be between 50 to 110 mm. In some embodiments, the length of each tubular transducer may be between 0.9 to 30 mm. In some embodiments, the length of each tubular transducer may be between 1 to 30 mm. In some embodiments, the length of each tubular transducer may be between 3 to 30 mm. In some embodiments, the length of each tubular transducer may be between 10 to 30 mm. In some embodiments, the length of each tubular transducer may be between 20 to 30 mm. In some embodiments, the length of each tubular transducer may be between 15 to 25 mm. In some embodiments, the length of each tubular transducer element may be between 80 to 100 mm. In some embodiments, the length of each tubular transducer may be about 20 mm. In some embodiments, the length of each tubular transducer may be about 30 mm.

The outer diameter of the tubular transducers may be between 2.7 to 11 mm and the inner diameter may be between 1.8 to 10 mm. In some embodiments, the outer diameter of the tubular transducers may be between 5.4 to 7.7 mm and the inner diameter may be between 3.6 to 6.6 mm. In some embodiments, the outer diameter of the tubular transducers may be between 5 to 8 mm and the inner diameter may be between 3 to 6 mm. In some embodiments, the outer diameter of the tubular transducers may be between 5 to 7 mm and the inner diameter may be between 3 to 5 mm. In some embodiments, the outer diameter of the tubular transducers may be between 6 to 8 mm and the inner diameter may be between 4 to 6 mm.

The gaps length between transducers 120 may be between 0.9 to 22 mm. Transducers 120 of different lengths and/or outer diameters may be mounted on or within catheter 110. Furthermore, the gaps between transducers 120 may be of different lengths.

In some embodiments, transducers 120 which are flat (e.g., in the form of a flat rectangular or a disc) may be used. Such flat transducers may produce non-focused ultrasonic radiation. In such a configuration, at least one flat transducer may be mounted on or disposed within the catheter. A disc-shaped transducer may surround a section of the catheter. In using flat transducers, one may avoid energy drop over distance which may be caused when using tubular (i.e., radial) transducers, thereby allowing bladder wall treatment at higher intensities. However, flat transducers may not provide the multidirectional coverage provided by the tubular or radial ones. Thus, in some embodiments, several flat transducers may be mounted on or disposed within the catheter, while each transducer may be positioned to irradiate a different section of the bladder wall. In one optional configuration, the flat transducers may be arranged around a section of the catheter to form various three-dimensional shapes such as a three-dimensional triangle or a cube. Such forms may be achieved by using, for example, three or four flat rectangular transducers correspondingly.

In some embodiments, the length of a flat transducer may be between 2.7 to 16.5 mm. In some embodiments, the length of a flat transducer may be between 6 to 13.5 mm. In some embodiments, the length of a flat transducer may be between 2.7 to 10.5 mm. In some embodiments, the length of a flat transducer may be between 9 to 16.5 mm. In some embodiments, the length of a flat transducer may be between 2.7 to 6 mm. In some embodiments, the length of a flat transducer may be between 13 to 16.5 mm.

In some embodiments, the width of a flat transducer may be between 1.8 to 11 mm. In some embodiments, the width of a flat transducer may be between 1.8 to 6.5 mm. In some embodiments, the width of a flat transducer may be between 6.5 to 11 mm. In some embodiments, the width of a flat transducer may be between 4 to 9 mm. In some embodiments, the width of a flat transducer may be between 1.8 to 5 mm. In some embodiments, the width of a flat transducer may be between 8 to 11 mm.

In some embodiments, the thickness of the flat transducer may be between 2 microns to 4 mm. In some embodiments, the thickness of the flat transducer may be between 0.2 mm to 4 mm. In some embodiments, the thickness of the flat transducer may be between 0.2 mm to 1 mm. In some embodiments, the thickness of the flat transducer may be between 1 mm to 4 mm. In some embodiments, the thickness of the flat transducer may be between 1 mm to 2 mm. In some embodiments, the thickness of the flat transducer may be between 200 microns to 500 microns. In some embodiments, the thickness of the flat transducer may be between 3.5 mm to 4 mm.

In some embodiments, transducers 120 may be intermittently operated at a relatively low and a relatively high frequency, such that the relatively low frequency creates cavitation and the relatively high frequency heats bladder 190. This may be achieved by operating transducers 120 in their relatively low harmonic and their relatively high harmonic, respectively. Alternatively, this may be achieved by different ones of transducers 120 having a different resonant frequency at their first harmonic.

Figure 2:
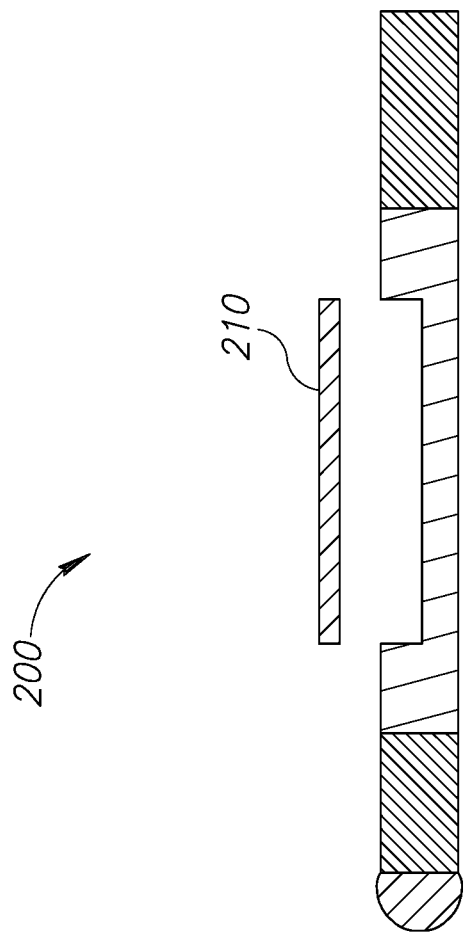
FIG. 2A shows a side view and partially exploded of a distal portion of an exemplary urinary catheter, which incorporates a flat rectangular ultrasonic transducer, according to another embodiment.
FIG. 2B shows a top view of the flat rectangular ultrasonic transducer of FIG. 2A.

Reference is now made to FIGS. 2A and 2B. FIG. 2A shows a side view and partially exploded of a distal portion of an exemplary urinary catheter 200, which incorporates a flat rectangular ultrasonic transducer 210 (or simply 'transducer 210'), according to another embodiment. FIG. 2B shows a top view of flat rectangular ultrasonic transducer 200 of FIG. 2A. Transducer 210 is formed as a flat rectangular. Transducer 210 may be integrated with catheter 200 by removing an outer section of the distal portion of catheter 200 and replacing it with transducer 210. Such integration of catheter 200 and transducer 210 may allow easier insertion of the device through the urethra.

Since the transducers of a device according to embodiments, may be in a distance of a few centimeters from the bladder internal surface, high electric power may be delivered to the transducers in order to receive a high acoustic output close to the inner surface of the bladder wall. Thus, in some embodiments, the transducers may be wired in a separate manner (i.e., each separately coupled with the power source), in order to allow exciting each of the transducers separately. A separate excitation of the transducers may allow using lower electric energy.

Referring now to FIG. 1, balloon 130 may enclose transducers 120, inter alia, in order to distance transducers 120 from any cavitation effects that may be formed as a result of their operation. In some embodiments, transducers 120 may be internally enclosed by balloon 130 by disposing transducers 120 inside balloon 130. Optionally, transducers 120 may be disposed upon a portion of catheter 110 which is enclosed by balloon 130.

In some embodiments, balloon 130 may have a maximal diameter which is above 0 and up to 11 cm. In some embodiments, balloon 130 may have a diameter which is above 0 and up to 5.5 cm. In some embodiments, balloon 130 may have a maximal diameter which is between 5.5 and 11 cm. In some embodiments, balloon 130 may have a maximal diameter which is between 2.5 and 8 cm. In some embodiments, balloon 130 may have a maximal diameter which is above 0 and up to 3 cm. In some embodiments, balloon 130 may have a maximal diameter which is between 8 and 11 cm.

In some embodiments, balloon 130 may have a length which is between 1 cm and 10 cm. In some embodiments, balloon 130 may have a length which is between 3 cm and 7.5 cm. In some embodiments, balloon 130 may have a length which is between 1 cm and 4 cm. In some embodiments, balloon 130 may have a length which is between 7 cm and 10 cm. In some embodiments, balloon 130 may have a length which is between 1 cm and 5.5 cm. In some embodiments, balloon 130 may have a length which is between 5.5 cm and 10 cm.

Balloon 130 may secure the distal portion of catheter 110 in bladder 190, once inserted within, similarly to a standard Foley catheter balloon. In some embodiments, device 100 may include an additional balloon (i.e., in addition to balloon 130), configured to secure the distal portion of catheter 110 in bladder 190.

Balloon 130 may incorporate (i.e., when transducers 120 are disposed inside balloon 130) and/or cover transducers 120. Hence, in deflated state, during insertion through a urethra, balloon 130 may protect the urethra passage and may allow for a more smooth and easy insertion of device 100.

As described above, in order to increase therapeutic delivery to the bladder tissue, ultrasound cavitation bubbles should form in the fluid near the bladder internal surface. Thus, balloon 130 may be configured to be filled with an acoustic coupling medium (not shown), in which, cavitation bubbles are less likely to form. This may ensure that bubble formation will not occur adjacent to transducers 120, thereby ultrasound energy directed to an internal surface of bladder 190 may not be blocked. On the other hand, the space between balloon 130 and bladder 190 may be filled with the therapeutic fluid which may include therapeutic agent 145. In the therapeutic fluid, cavitation bubbles 185 may be formed, as it contains dissolved gas. The difference in cavitation threshold between the acoustic coupling medium in the balloon and the fluid that fills the space between the balloon and the bladder may distance the cavitation phenomenon from the transducer. This may allow bringing cavitation effects closer to the internal surface of bladder 190 and facilitate ultrasound delivery of therapeutic agent 145.

In some embodiments, the therapeutic fluid may include cavitation booster, which may encourage cavitation, for example, contrast agents, such as microbubbles, micro-particles, nano-particles, liposomes, or gas, such as high concentration of gases (e.g., oxygen and argon). This may increase the likelihood of forming cavitation in the space between balloon 130 and the internal surface of bladder 190, thereby improving the transfer of therapeutic agent 145 into bladder 190. In case microbubbles are used, transducers 120 may be activated at a frequency between 0.7 to 10 Megahertz. In some embodiments, transducers 120 may be activated at a frequency between 0.9 to 2.5 Megahertz.

In some embodiments, in which transducers 120 are disposed inside balloon 130, one may use a cold acoustic coupling medium (e.g., of a temperature between 5 to 20 Celsius degrees) for the purpose of cooling transducers 120. When delivering high electric power to transducers 120, which may result in a high heat build-up, bladder 190 and/or transducers 120 may be at risk of being damaged (e.g., by causing hyperthermia). Thus, cooling of transducers 120 may be required. In some embodiments, the cold acoustic coupling medium may, in addition, be circulated within balloon 130 via inlet channel 160 and outlet channel 165. In some embodiments, device 100 may incorporate a temperature sensor configured to monitor the temperature of transducers 120 and ensure that the temperature of transducers 120 does not exceed a predefined threshold temperature. The threshold of the temperature may be, for example, between 90° and 250° Celsius.

The thickness of standard balloons used in prior art intravesical treatments may range between $2 \cdot 10^{-2}$ and $10 \cdot 10^{-2}$ mm. Since the disclosed ultrasonic therapeutic agent delivery utilizes cavitation effects, and in some cases, significant cavitation effects, a thicker balloon may be required in order to prevent damage or holes in the balloon. Thus, in some embodiments, the thickness of balloon 130 may be between $2 \cdot 10^{-2}$ mm and $2 \cdot 10^{-1}$ mm. In some embodiments, the thickness of balloon 130 may be between $2 \cdot 10^{-2}$ and $10 \cdot 10^{-2}$ mm. In some embodiments, the thickness of balloon 130 may be above $10 \cdot 10^{-2}$ and up to $2 \cdot 10^{-1}$ mm. In some embodiments, the thickness of balloon 130 may be above $10 \cdot 10^{-2}$ and up to $1.5 \cdot 10^{-1}$ mm. In some embodiments, the thickness of balloon 130 may be between $1.5 \cdot 10^{-1}$ and $2 \cdot 10^{-1}$ mm. In some embodiments, the thickness of balloon 130 may be between $1.8 \cdot 10^{-1}$ and $2 \cdot 10^{-1}$ mm.

The power source of console 195 may supply power to the transducers 120 via electrical wires 180. The pump of console 195 may pump the acoustic coupling medium out of balloon 130. In some embodiments, the pump may be used to circulate the acoustic coupling medium, e.g., via inlet channel 160 and outlet channel 165, in order to cool transducers 120.

A device according to some of the disclosed embodiments may further include a rotating unit configured to rotate the one or more ultrasonic transducers mounted on or disposed within the ultrasonic catheter when the device is placed within the urinary bladder. Such rotating unit may be required, for example, when using a single or few ultrasonic transducers which may not ultrasonically irradiate a sufficient portion or a desired portion of the bladder.

When device 100 is introduced into bladder 190, balloon 130 may be filled with the acoustic coupling medium and transducers 120 may be activated to direct ultrasound waves 125 towards the internal surface of bladder 190. Cavitation bubbles 185 may be formed in the delivered therapeutic fluid, which may include therapeutic agent 145, adjacent to the internal surface of bladder 190. Little or no cavitation bubbles may be formed in proximity to transducers 120. Thereby, increasing the permeability of bladder 190 and facilitating the delivery of therapeutic agent 145 to bladder 190.

The distance between the balloon and the bladder internal surface may be of importance. This is since cavitation bubbles 185 may form in the fluid there between. A distance between the balloon and the internal surface of the bladder which is too large, may decrease the likelihood of cavitation bubbles forming adjacent to the bladder internal surface and thus interacting with it. A smaller distance between the balloon and the bladder internal surface may increase the chances that cavitation bubbles will form adjacent to the bladder, and increase delivery of therapeutic agents to the bladder. On the other hand, if the balloon touches the bladder internal surface, this may prevent cavitation bubbles generation at the contact areas since at such areas there may be no fluid in which cavitation may form. A small distance between the balloon and the bladder (e.g., a thin layer of fluid between the balloon and the bladder) will maximize the formation of cavitation bubbles that interact with the bladder wall.

In some embodiments, a balloon may be designed such that its inflated configuration allows varying distances from the bladder internal surface, in specific areas. This design may be utilized in order to achieve varying degrees of cavitation and/or eliminate cavitation of these specific areas.

Figure 16:
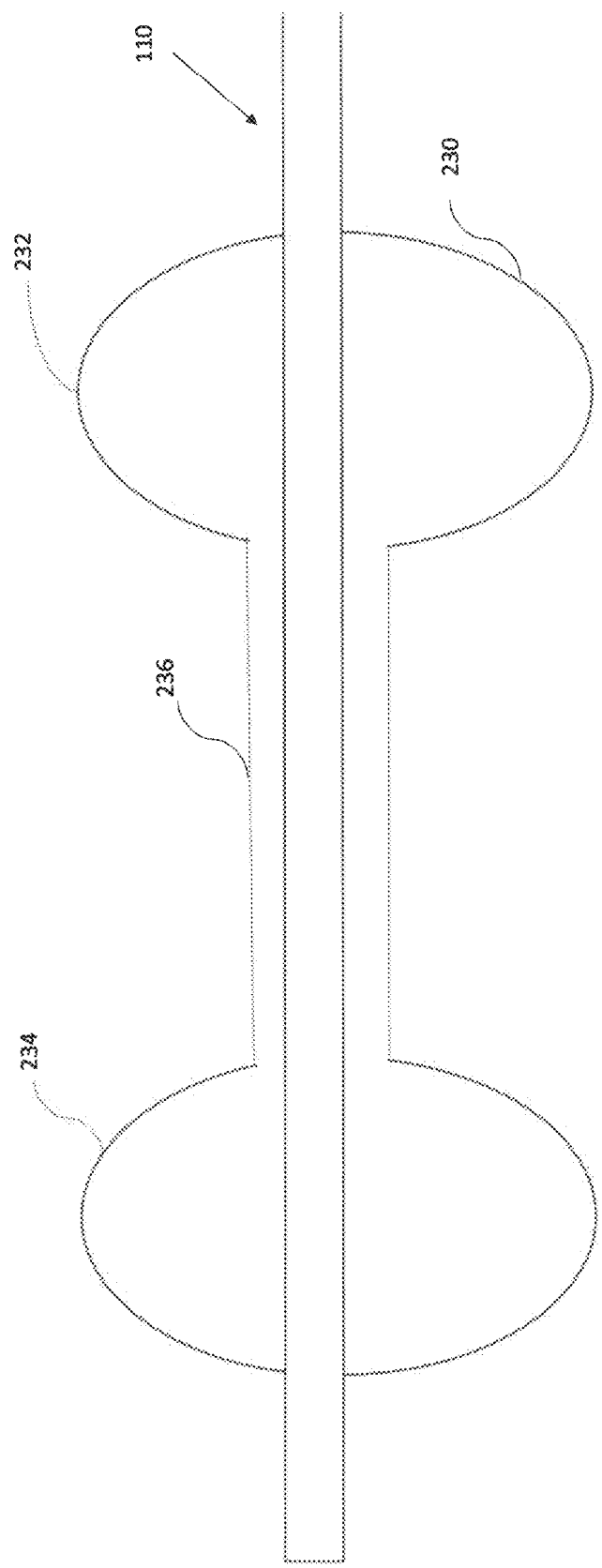
FIG. 16 shows the configuration of a balloon having a specified shape.

In some embodiments, the diameter of the inflated balloon 130 may vary along a longitudinal axis of balloon 130. More specifically, in some embodiments, see, for example, FIG. 16, balloon 130 may have certain sections that may inflate to different sizes (i.e., having different diameters). For example, balloon 130 may have a distal portion which may inflate to a diameter which is larger than the diameter of its middle portion, and its middle portion may inflate to a diameter which is larger than its proximal portion diameter. In such a configuration, the shape of balloon 130 may be shaped similarly to the shape of the bladder, but smaller in size, advantageously, as small as possible without the balloon touching the bladder internal surface. Other optional shapes may be a sphere, an elongated cylinder, an elongated cylinder as in FIG. 16 having two lateral portions 232 and 234 which are larger in diameter than a middle portion 236, an inverted pyramid, a conical shaped balloon or the like. In some embodiments the balloon may have an asymmetric shape. In some embodiments, the balloon may not touch the internal surface of the bladder. In some embodiments, the balloon may touch the internal surface of the bladder. In some embodiment the balloon shape may be designed such that it touches the bladder wall at a certain area such that it eliminates drug delivery to this area in the bladder. For example, a balloon which has a shape of an elongated cylinder having two lateral sides which are larger in diameter than its middle portion may touch the bladder internal surface by its two lateral portions, and the therapeutic fluid may flow or reside there between, in a space formed between the middle portion of the balloon and the bladder internal surface. For yet another example, in order to deliver Botox to the bladder and avoid its delivery to the trigone of the bladder, the balloon may be designed to touch the trigone (elongated cylinder designed to thereby eliminating drug delivery to the trigone.

In some embodiments, multiple balloons 130 of various shapes may be used. In such embodiments, each of multiple balloons 130 may enclose one or more of transducers 120.

Figure 3:
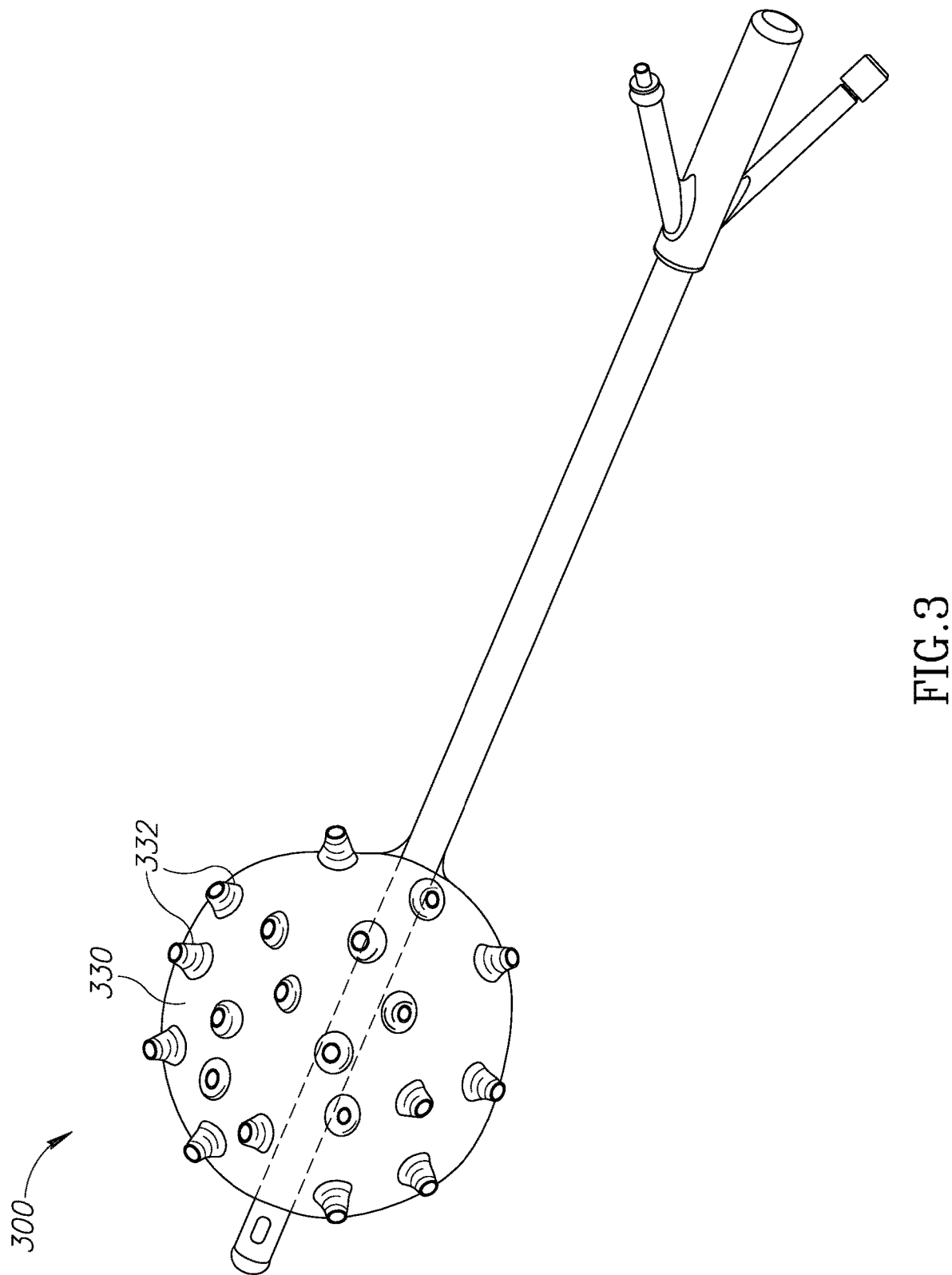
FIG. 3 shows a perspective view of an exemplary device according to another embodiment.

Reference is now made to FIG. 3, which shows a device 300, in accordance with another embodiment. Device 300 is substantially similar to device 100 of FIG. 1 but further includes spacers 332. Optionally, balloon 330, corresponding to balloon 130 of FIG. 1, is equipped with spacers 332 (e.g., bulges) which are configured to distance balloon 330 from a bladder wall (not shown) allowing therapeutic fluid to reside between balloon 330 and the bladder wall. Optionally, a height of at least some of spacers 332 may range between 0.01-20 millimeters (mm). Optionally, spacers 332 may be of equal heights. Alternatively, spacers 332 may differ in heights. Optionally, spacers 332 may be disposed upon and inflated with balloon 330. Alternatively, spacers 332 may be part of balloon 330, namely—portions of the balloon which, when the balloon is inflated, inflate to form bulges. Optionally, in order to prevent the bladder wall from collapsing in between the spacers 332, a distance between each spacer (e.g., bulge) and its closest neighboring spacer should not exceed 1 centimeter. Optionally, the distance between neighboring spacers 332 is less than 1.5, 1, or 0.5 centimeters. Alternatively the spacers may be made of ridges that encircle the balloon but are but an integral part of it.

Figure 4:
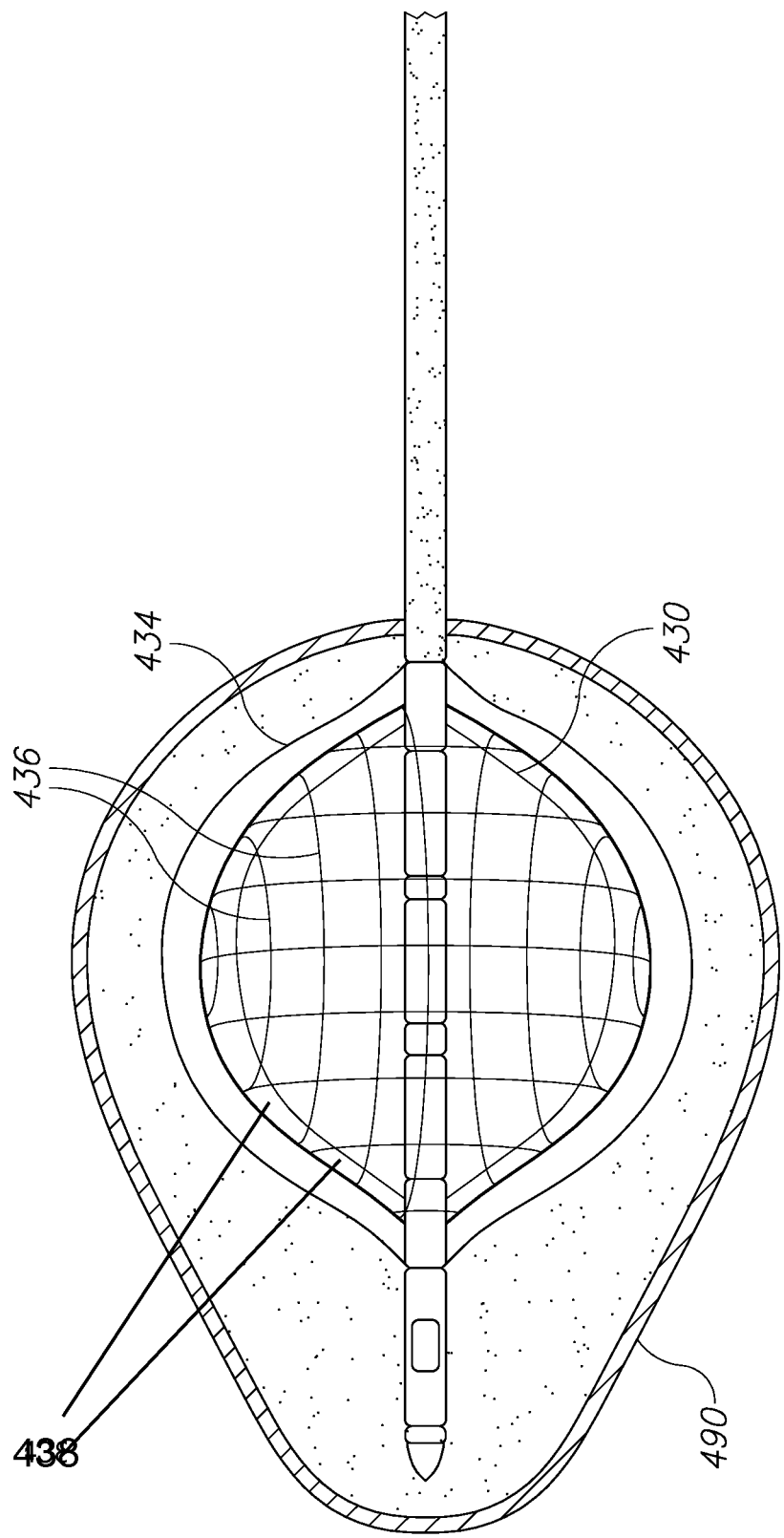
FIG. 4 shows a top view and partially transparent of an exemplary device disposed within a urinary bladder, according to another embodiment.

Reference is now made to FIG. 4, which shows a top view and partially transparent of an exemplary device 400 disposed within a urinary bladder 490, in accordance with another embodiment. Device 400 is substantially similar to device 100 of FIG. 1 with the notable difference that device 400 further includes a structure 434 placed around balloon 430, corresponding to balloon 130 of FIG. 1. Optionally, structure 434 may expand upon expansion of balloon 430. Structure 434 may trap cavitation nuclei (seeds) and increase cavitation phenomenon in the therapeutic fluid. Structure 434 may be in a form of a net or a mesh of wires 436. Examples of suitable materials include: plastic, nitinol, stainless steel, nylon, HDPE, polyethylene, cobalt based alloys, PEEK and the like. Optionally, structure 434 may entrap air bubbles, so when the user starts the treatment these air bubbles may serve as cavitation nuclei and thus may reduce significantly the cavitation threshold and increase cavitation intensity. Optionally, structure 434 may serve to distance balloon 430 from a bladder wall 490. This may facilitate reducing a distance between the balloon 430 and a bladder wall 498 to a minimal value limited by a thickness of wires 436. In this case the cavitation may take place only in the vicinity of the bladder wall and its efficiency will be maximal. Since the usage of the net may reduce the cavitation threshold, this may allow lower acoustic output thus reducing the risk of adverse effects. In some embodiments, the thickness of wires 436 may be between 0.1 mm to 1 mm, 0.1 mm to 0.8 mm, 0.1 mm to 0.7 mm, 0.1 mm to 0.6 mm, 0.1 mm to 0.5 mm, 0.2 mm to 0.6 mm, 0.3 mm to 0.8 mm, 0.3 mm to 0.6 mm, or 0.4 mm to 0.6 mm. Each possibility represents a separate embodiment of the present invention. In some embodiments, the thickness of the wires may vary between different areas of the net.

Optionally, openings 438 in the net or mesh are big enough to allow passage of fluid through such openings. Optionally, openings 438 are small enough to prevent the bladder wall from collapsing into the openings 438. In some embodiments, a diameter of openings 438 may be between 50 micrometers to 2 millimeters, 50 micrometers to 1.5 millimeters, 50 micrometers to 1 millimeter, 100 micrometers to 2 millimeters, 100 micrometers to 1.5 millimeters, or 100 micrometers to 1 millimeter. Each possibility represents a separate embodiment of the present invention. Optionally diameters of openings 438 may vary between different portions/areas of the net or mesh. For a non-limiting example, specific areas of the net or mesh may include openings 438 in the net or mesh that allow portions of the bladder wall to collapse into the openings and contact the surface of the balloon, thereby preventing cavitation bubbles from forming in these portions of the bladder wall.

Reference is now made to FIG. 5, which shows a device 500, in accordance with another embodiment. Device 500 is substantially similar to device 400 of FIG. 4 with the notable difference that device 500 further includes spacers 532 corresponding to spacers 332 of FIG. 3.

Figure 5A:
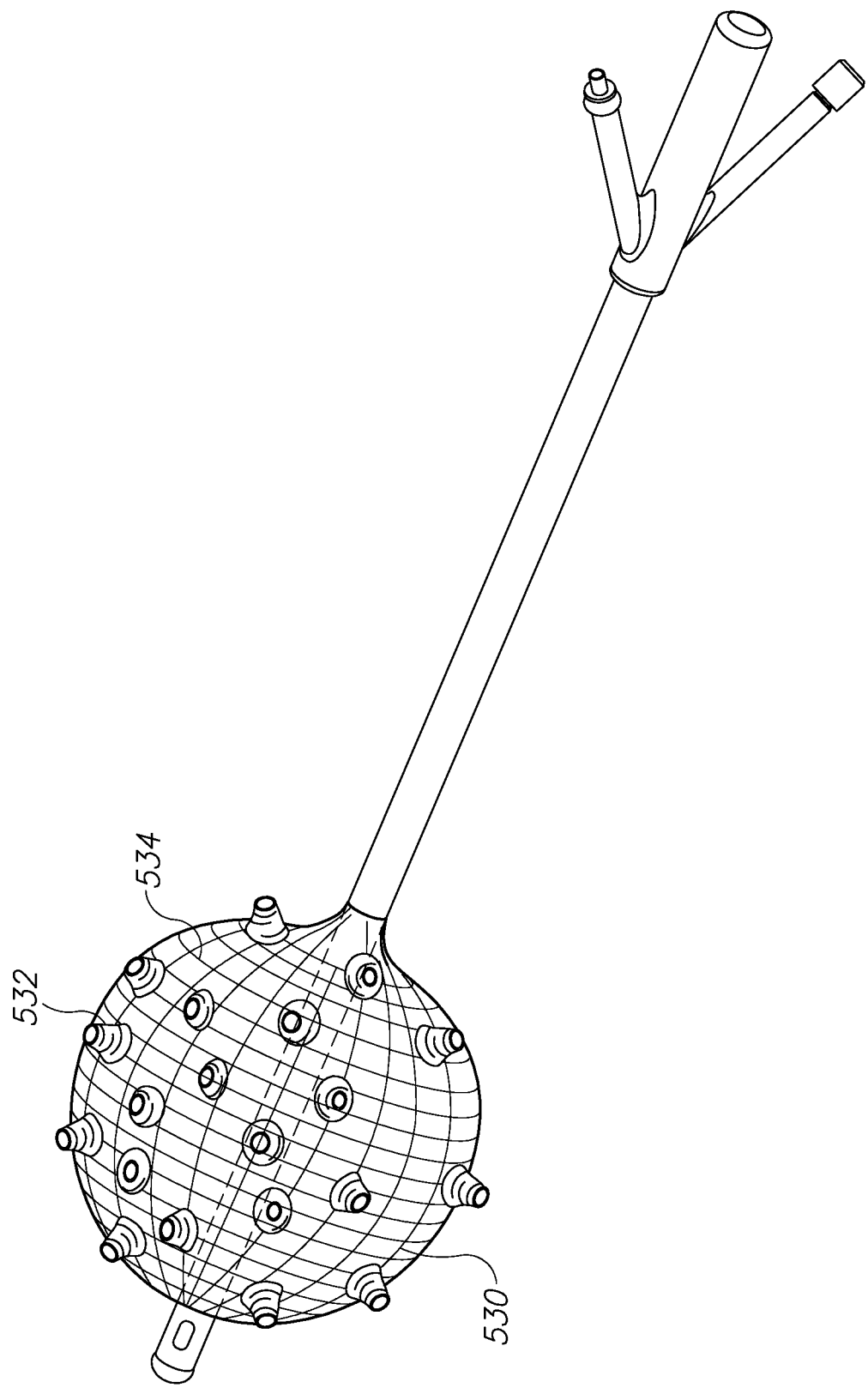
FIG. 5A shows a perspective view of the device of FIG. 1, according to another embodiment.
Figure 5B:
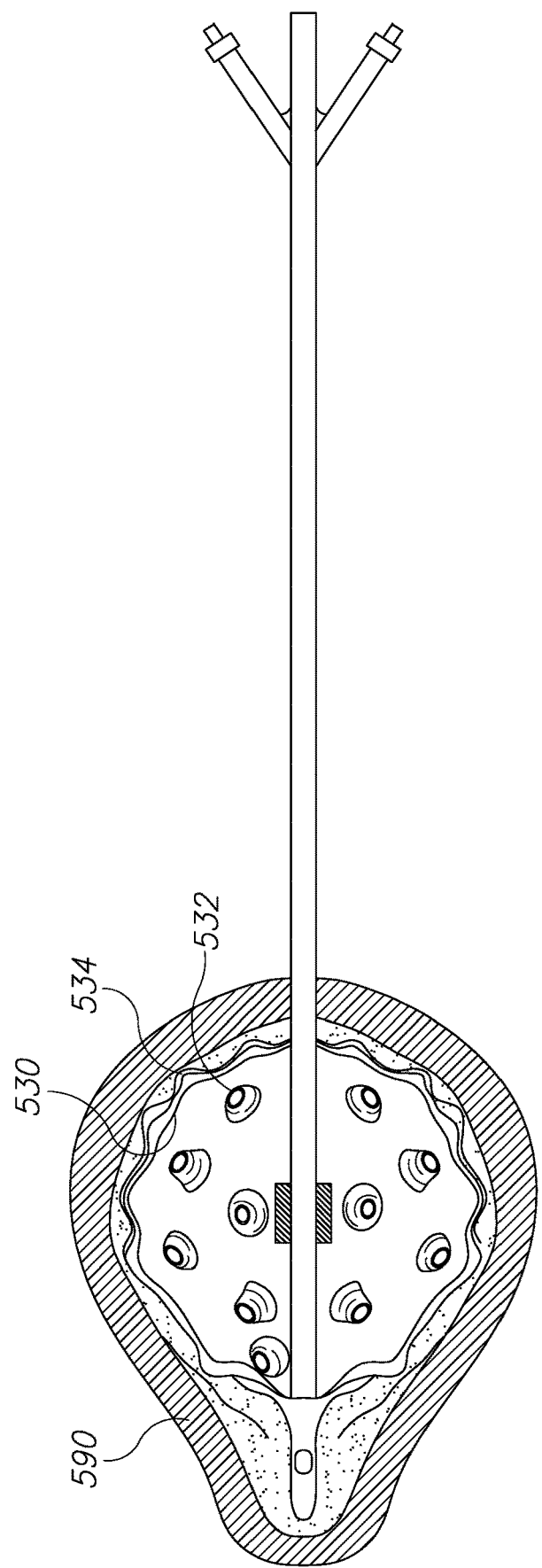
FIG. 5B shows a top view and partially transparent of the device of FIG. 5A disposed within a urinary bladder, according to an embodiment.

Reference is now made to FIG. 5B, which shows a top view and partially transparent of device 500 of FIG. 5A disposed within a urinary bladder 590 in accordance with an embodiment.

Figure 6:
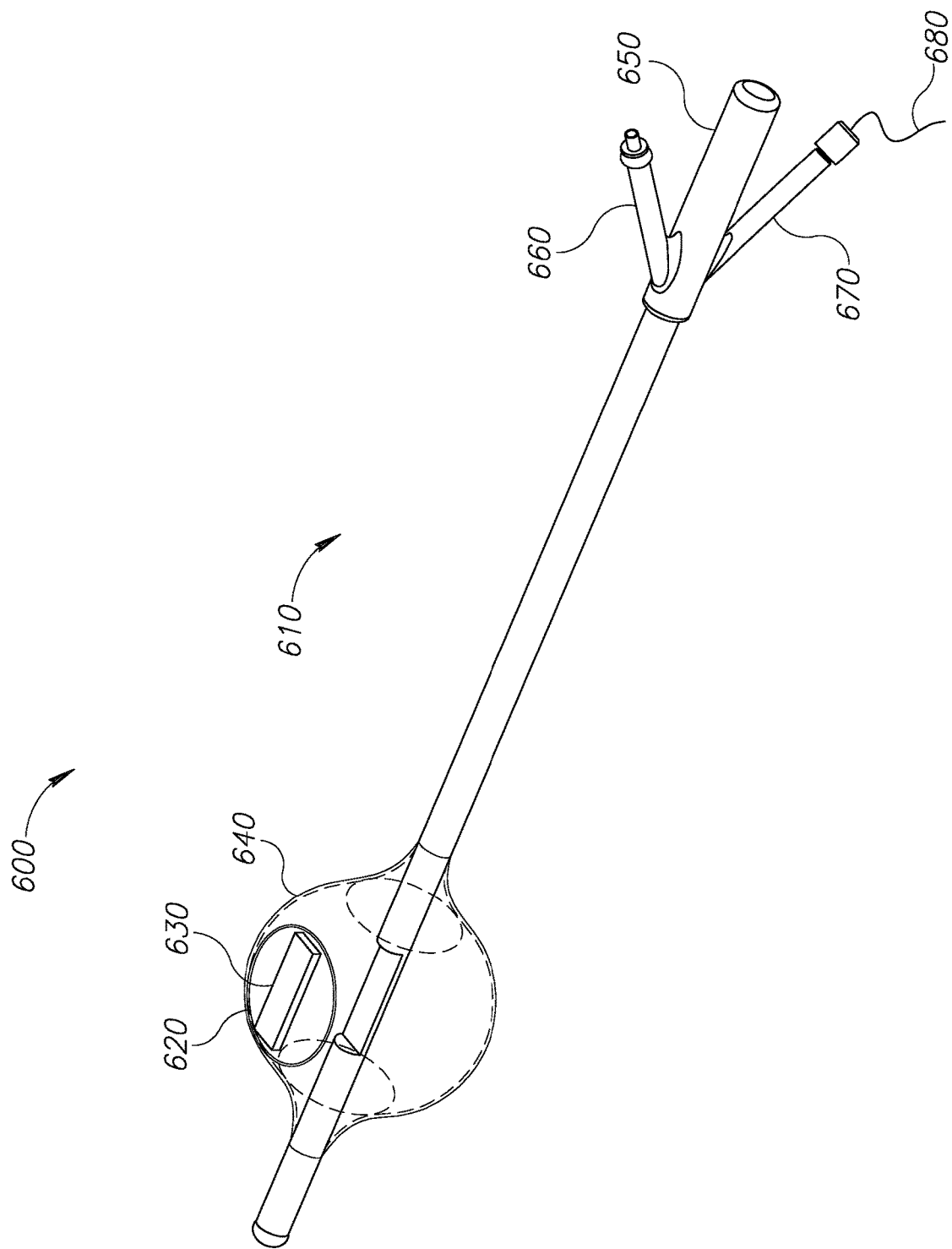
FIG. 6 shows a perspective view of an exemplary device according to a further embodiment.
Figure 7:
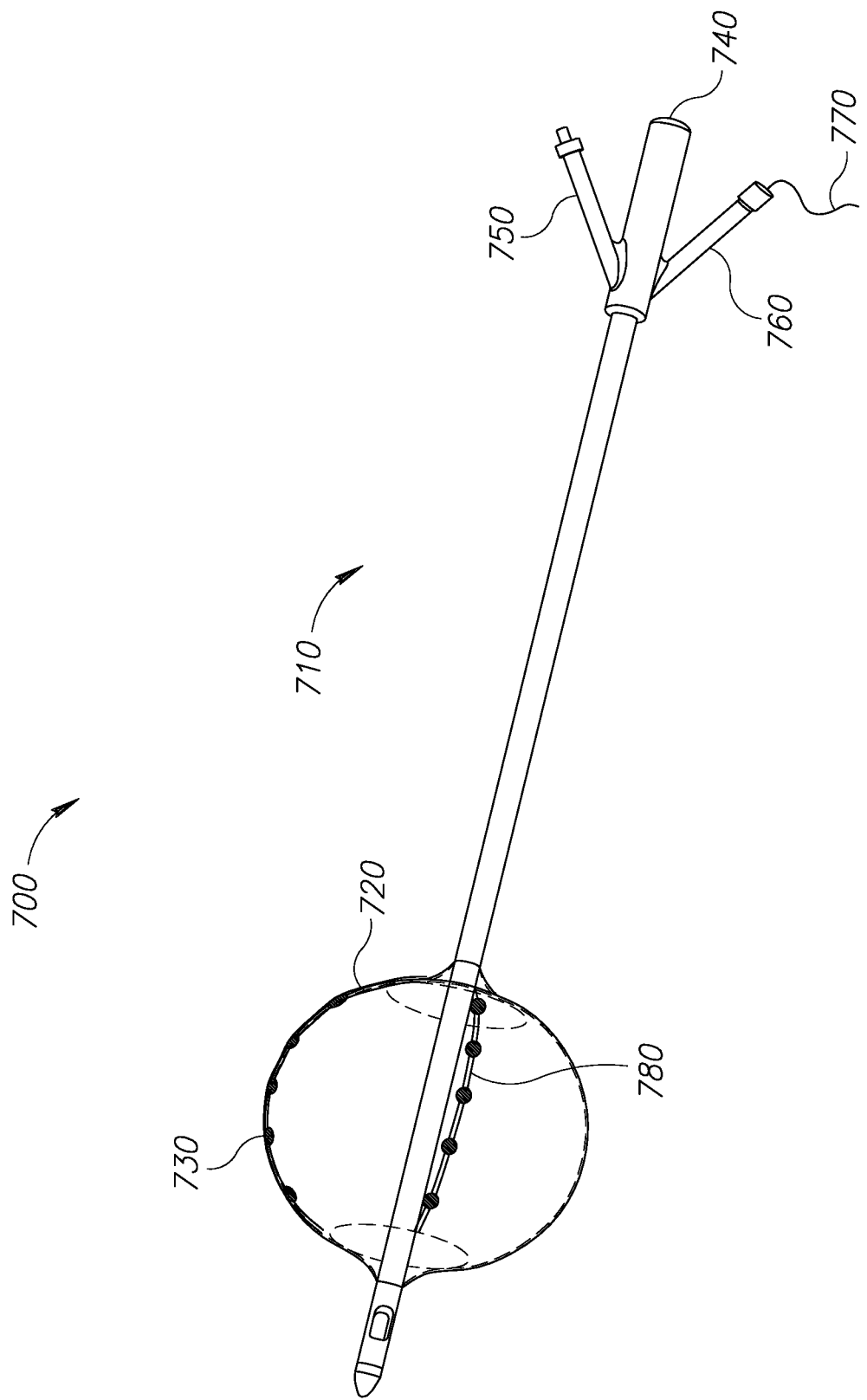
FIG. 7 shows a perspective view of an exemplary device according to yet another embodiment.

Reference is now made to FIGS. 6 and 7. FIG. 6 shows a perspective view of an exemplary device 600 according to a further embodiment. FIG. 7 shows a perspective view of an exemplary device 700 according to yet another embodiment.

Device 600 may include a urinary catheter 610, a balloon 640 and an ultrasonic transducer 630. Device 600 may be similar to device 100 of FIG. 1 with the required modifications. Urinary catheter 610 may be similar to catheter 110 and may include a main channel 650, an inlet channel 660, an outlet channel 670 and electrical wires 680. Balloon 640 may include a dent 620 on which ultrasonic transducer 630 is mounted. Ultrasonic transducer 630 of exemplary device 600 is formed as a flat rectangular.

Device 700 may include a urinary catheter 710, a balloon 730 and a plurality of ultrasonic transducers 720. Device 700 may be similar to device 100 of FIG. 1 with the required modifications. Urinary catheter 710 may be similar to catheter 110 and may include a main channel 740, an inlet channel 750, an outlet channel 760 and electrical wires 770. Ultrasonic transducers 720 may be relatively small in size (i.e., to allow numerous such transducers) and may be scattered on the surface of balloon 730. For example, ultrasonic transducers 720 may be interlaced on wires which may encircle at least a portion of balloon 730.

As shown, in devices 600 and 700, transducers 630 and 730, correspondingly, are mounted on balloons 640 and 720, correspondingly. Thus balloons 640 and 720 may be used to position transducers 630 and 730, correspondingly, closer to the bladder internal surface. In such configurations, the transducers may be activated at lower frequencies in comparison to the configurations in which the transducers are mounted on or disposed within the catheter.

Figure 8:
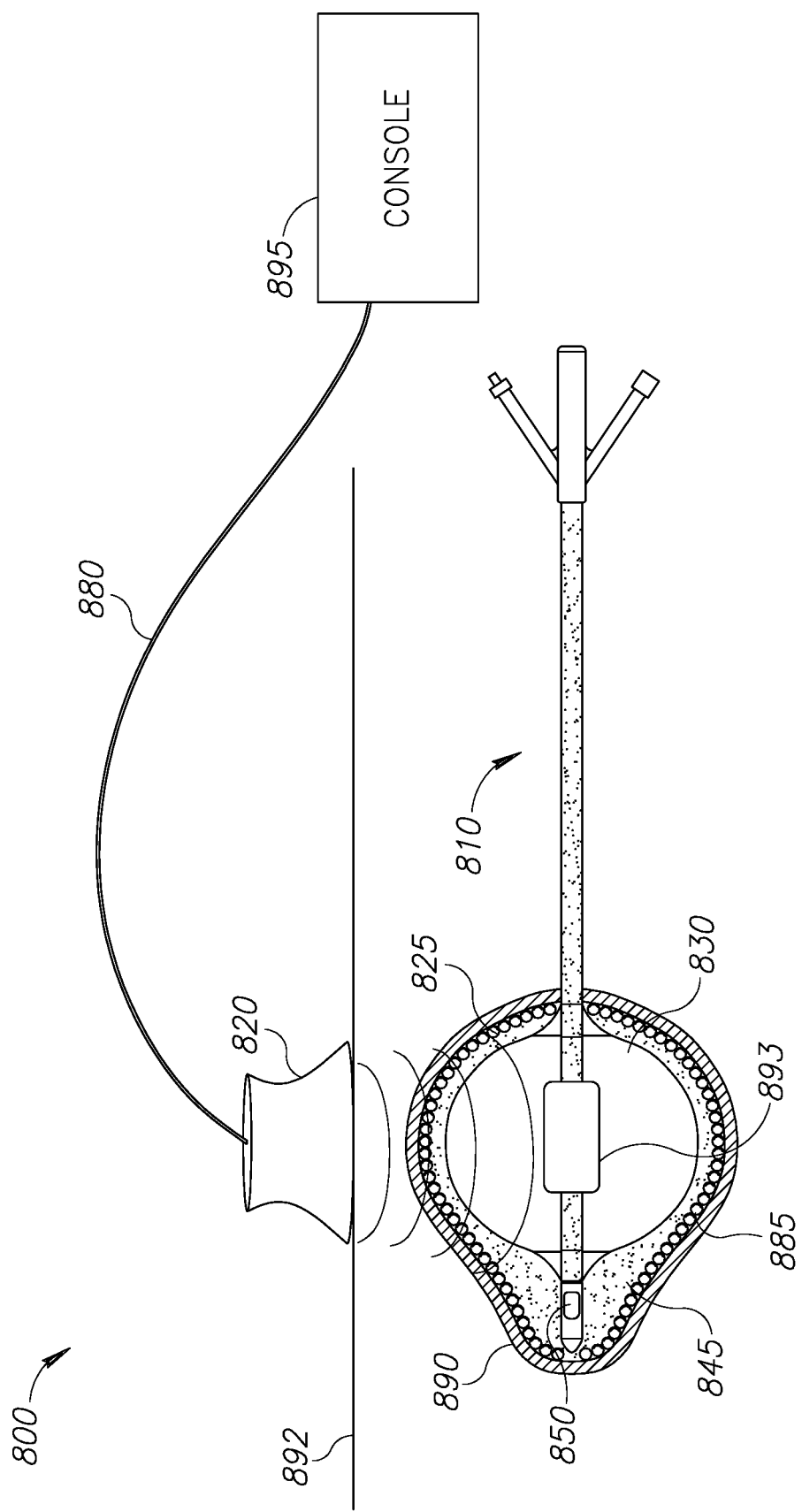
FIG. 8 shows a top view and partially transparent of an exemplary system including a device disposed within a urinary bladder, according to an embodiment.

Reference is now made to FIG. 8 which shows a system 800, in accordance with another embodiment. System 800 is substantially similar to device 100 described in FIG. 1 with the notable difference that one or more ultrasonic transducers 820, corresponding to ultrasonic transducers 120 of FIG. 1 above, are positioned externally to the urinary bladder 890, rather than disposed within a balloon 830 corresponding to balloon 130 as shown in FIG. 1. Optionally, one or more ultrasonic transducers 820 are positioned on a skin surface 892 of a body in close proximity to bladder 890. Similarly to transducers 120, one or more transducers 820 may be configured to emit ultrasonic waves 825 towards the internal surface of bladder 890.

System 800 may further include a urinary catheter 810 (or simply 'catheter 110') corresponding to urinary catheter 810 of FIG. 1. Optionally, balloon 830 may be mounted on a distal portion of catheter 810. System 800 may further include electrical wires 880 corresponding to electrical wires 180 of FIG. 1. System 800 may be operatively coupled with a console 895, via electrical wires 880. Optionally, console 895 may include a power source. Electrical wires 880 may operatively couple one or more transducers 820 with the power supply of console 895. Optionally, console 895 may further include one or more pumps (not shown). One or more pumps of console 895 may pump an acoustic coupling medium out of balloon 830.

After system 800 is introduced into bladder 890, balloon 830 may be filled with the acoustic coupling medium and transducers 820 located externally to bladder 890 may be activated to direct ultrasound waves 825 towards the internal surface of bladder 590. Optionally, therapeutic fluids which includes therapeutic agent 845 may be introduced to urinary bladder 890 via an opening 850 positioned at the distal portion of catheter 810. Cavitation bubbles 885 may be formed in the delivered therapeutic fluid, which may include therapeutic agent 845, adjacent to the internal surface of bladder 590. Little or no cavitation bubbles may be formed in proximity to transducer 820. Accordingly, system 800 may increase permeability of bladder 890 and may further facilitate delivery of therapeutic agent 845 to bladder 890.

In another embodiment, there is provided a system (not shown) substantially similar to device 100 with the notable difference that in addition to transducers 120 of device 100 the system may further include one or more transducers 820 of system 800.

A kit including a urinary catheter, at least one ultrasonic transducer and a balloon as disclosed herein (e.g., catheter 110, transducers 120 and balloon 130 of device 100 of FIG. 1) and a first reservoir, schematically shown at 116 containing an acoustic coupling medium is further disclosed. The acoustic coupling medium may be used with the urinary catheter in order to inflate the balloon. The acoustic coupling medium may be a cold acoustic coupling medium as disclosed herein, for example, with respect to device 100 of FIG. 1. In some embodiments, the kit may further include a second reservoir, schematically shown at 118 including a therapeutic fluid, which may include or may not include a therapeutic agent 145, as herein disclosed, for example, with respect to device 100 of FIG. 1. In some embodiments, the therapeutic fluid may include a cavitation booster, as herein disclosed, for example, with respect to device 100 of FIG. 1.

Figure 9:
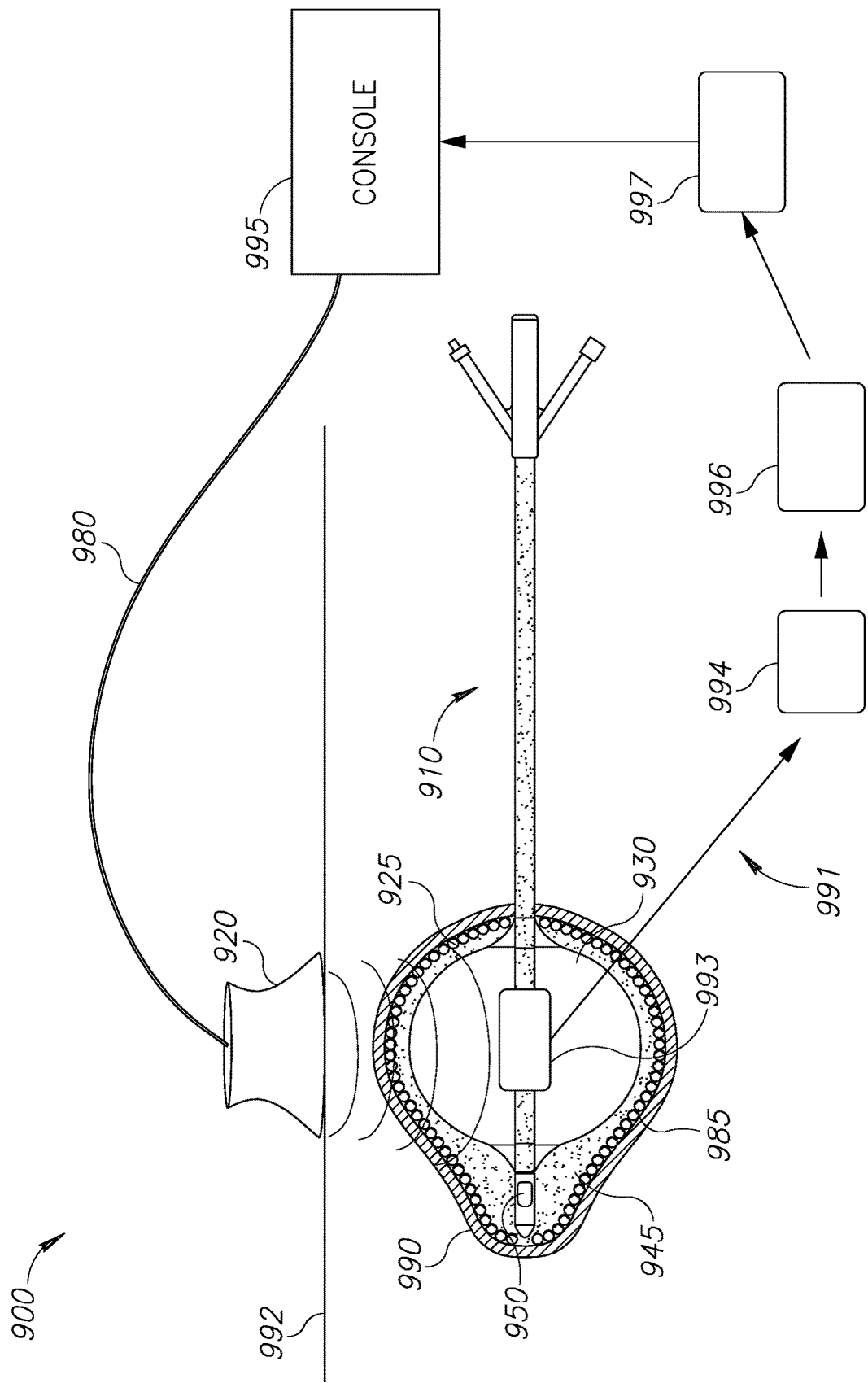
FIG. 9 shows a top view and partially transparent of an exemplary implementation of the system of FIG. 8, in accordance with another embodiment.

Reference is now made to FIG. 9 which shows a system 900, in accordance with another embodiment. System 900 is substantially similar to system 800 described in FIG. 8 with the notable difference that a cavitation monitor 991 is provided to communicate with ultrasonic transducers 920, corresponding to ultrasonic transducers 820 of FIG. 5 above.

Optionally, cavitation monitor 991, may include a detector transducer 993 (e.g., passive cavitation detector (PCD), hydrophone, to name a few) mounted on a distal portion of catheter 910, corresponding to catheter 810 of FIG. 8 above.

Optionally, detector transducer 993 may be disposed within a balloon 930 corresponding to balloon 830 of FIG. 5 above.

Optionally, detector transducer 993 may include a tubular piezoelement (not shown) installed at the distal portion of catheter 610. Due to the axial symmetry of the piezoelement the detector transducer 993 may receive acoustic signals from all directions along its length. It has 360° wide pattern directivity in the plane perpendicular to its axis, but its sensitivity is low in the axial direction. Alternatively or additionally, to achieve improved directivity in the axial direction, detector transducer 993 may include two flat piezoelements which possess pattern directivity having the maximum along the axial direction. Alternatively, detector transducer 993 may comprise a number of flat piezoelements arranged along the axial direction of catheter 910. The maximum of the pattern directivity of each piezoelement lies in the plane perpendicular to the surface of the piezoelement and respective intersection lies along its longitudinal direction. Each element may be connected to one of the inputs of a multiplexer (not shown). Its output is connected to the input of the preamplifier. The multiplexer is also connected to the computer system, which controls its work. So by switching between elements we can analyze if the cavitation is distributed homogeneously over the volume/interface of the bladder or there are areas where the cavitation is absent.

Detector transducer 993 may acquire acoustic emissions signals applied by ultrasonic transducers 920. Optionally, the signals received by detector transducer 993 may be amplified using a pre-amplifier 994 and may be further converted to digital signals by an analog to digital converter (ADC) 996.

Optionally, control unit 997 utilizes a computer program product comprising a non-transitory computer-readable storage medium having program code embodied thereon, the program code executable by at least one hardware processor to: receive a digital signal from analog to digital converter 996; compute a control signal from the digital signal; apply the control signal to control any of system 900 components. For a non-limiting example, the control signal may control cavitation formation by controlling power supply of console 995, corresponding to console 895 of FIG. 5. By these means, the control signal controls acoustic energy produced by ultrasonic transducers 920, which depends on electrical energy supplied to ultrasonic transducers 920.

Optionally, the control signal may be computed by comparing received digital signals to reference values, wherein each reference value represents a specific degree of cavitation activity. A level of the digital signal received by control unit 997 may depend on specific types of detector transducers 993 and preamplifier 994 used for a specific system 900. Optionally, reference values may be determined experimentally prior to treatment for each treatment setup and stored in the computer system memory (e.g., as a look up table). For a non-limiting example, when a digital signal received is found equal or slightly higher than the reference value, a control signal to maintain the electric power supplied to ultrasonic transducers 920 at a constant level is computed, thus maintaining a level of cavitation. For a non-limiting example, when the digital signal received is found to vary from the reference value, the computer computes a control signal to vary the electric power supplied to ultrasonic transducers 920 in order to increase/decrease cavitation level to reach the reference level.

Optionally, a control unit 997 may receive the digital signals and transmit the resulting controlling signal to the corresponding component using any standard wired and/or wireless communication protocol, such as USB, Bluetooth, or WiFi. Optionally, control unit 997 may further measure other parameters such as time of operation of system 900.

Optionally, a user-interface (not shown) may be provided allowing a user to define parameters. For example, the user may predefine a maximal time of operation for the system.

Optionally, control unit 997 may further control a duration of operation of system 600. Optionally, control signal to stop the operation of system 900 by stopping the electric power supplied to ultrasonic transducers 920 may be computed according to predetermined one or more parameters, such as total operation time of system 900, treatment time at a specific cavitation level, to name a few. Optionally, a control signal to stop the operation of system 900 may be computed at a specific value of an integral of $V^2$, which may be reached either at low intensity cavitation and longer treatment time or at high intensity cavitation and shorter treatment time. Optionally, specific parameters may be determined in accordance to a specific patient bladder parameters.

Figure 10A:
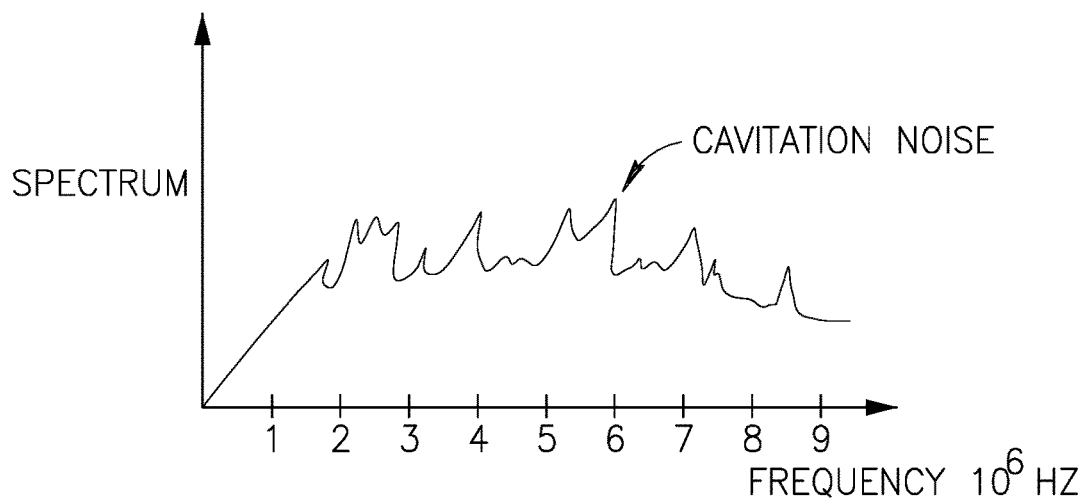
FIG. 10A is a graph showing a change in spectrum as a function of acoustic emission frequency.
Figure 10B:
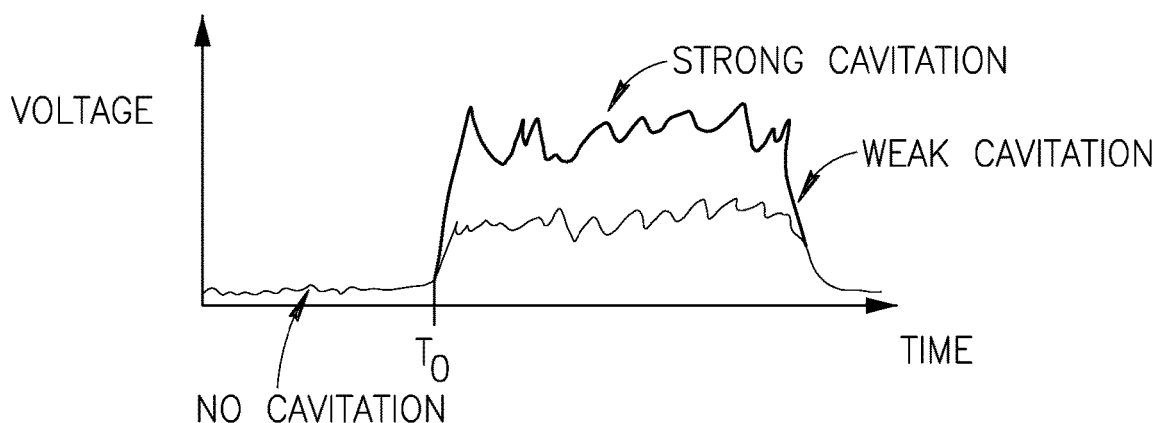
FIG. 10B is a graph showing a change of voltage as a function of time in a weak cavitation processes versus strong cavitation processes.
Figure 10C:
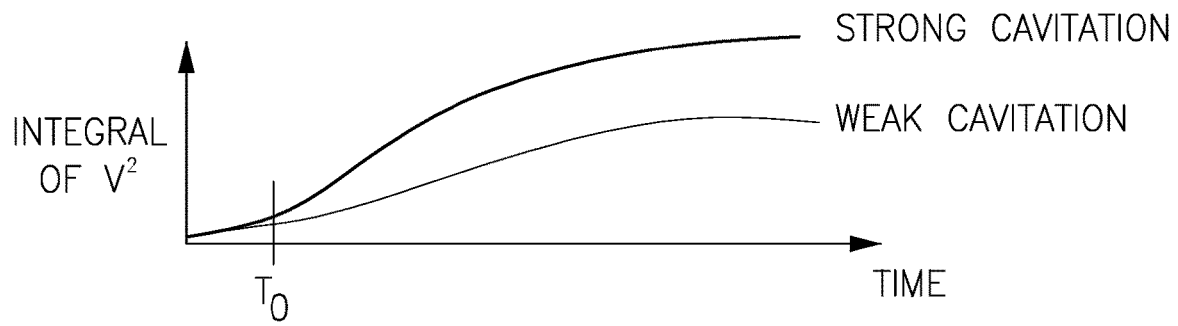
FIG. 10C is a graph showing a change of the square of a voltage as a function of time $V^2(t)$ in weak cavitation processes and strong cavitation processes.

Typically, acoustic emission produced by the cavitation event is characterized by a wide spectrum as is schematically shown in FIG. 10A. At the beginning, when acoustic pressure in the liquid is less than cavitation threshold there is no cavitation and noise level at an output of a pre-amplifier connected to a PCD is minimal. Acoustic pressure is increased until a sharp increase of the noise level is detected (at $T_0$) as is schematically illustrated in FIG. 10B, this indicates inertial cavitation initiation. Further increase of the acoustic pressure leads to increase of cavitation noise level. Cavitation bubbles strongly attenuate and scatter the high intensity acoustic signal emitted by an ultrasound transducer. The shock waves produced by collapsing bubbles are also scattered and attenuated by the bubbles within the cavitation cloud, therefore increase of cavitation noise level is not linearly proportional to the increase of acoustic energy emitted by the transducer. Alternative estimation of the intensity of cavitation may be achieved by measuring of root-square-mean voltage $V_{RMS}$ produced by the PCD, or the integral of the square of the voltage ($V^2$) as a function of time, produced by the PCD. The integral is proportional (though non-linearly) to the total acoustic energy produced by imploding bubbles and can also characterize the cavitation intensity. FIG. 10C is a schematic representation of integration results for the cases of strong and weak cavitation, respectively.

For yet another non-limiting example, during the operation of system 900, urinary bladder 990 is initially filled with therapeutic fluid 945, corresponding to therapeutic fluid 845 of FIG. 8, via an opening 950, corresponding to opening 850 of FIG. 8, positioned at the distal portion of catheter 910. Control unit may be configured to monitor the noise level during treatment and gradually increase electric power provided to ultrasonic transducers 920 if said noise level values are less than a specified reference value related to cavitation initiation. Optionally, when sub-harmonics, high harmonics and ultraharmonics frequencies are detected, control unit 997 computes a control signal to maintain the acoustic energy at constant level and continue treatment for a certain time duration. Alternatively, control unit 997 computes a control signal to continue to increase the acoustic energy until levels of the subharmonic or high harmonics, or their ratio, achieve predefined values. When a predefined value is achieved control unit 997 computes a control signal to maintain the acoustic pressure at the constant level and continue treatment for a predefined time duration. Alternatively, control unit 997 computes a control signal to continue increasing the acoustic energy until it will detect the appearance of the wideband noise which is the indication of inertial cavitation initiation.

Figure 11A:
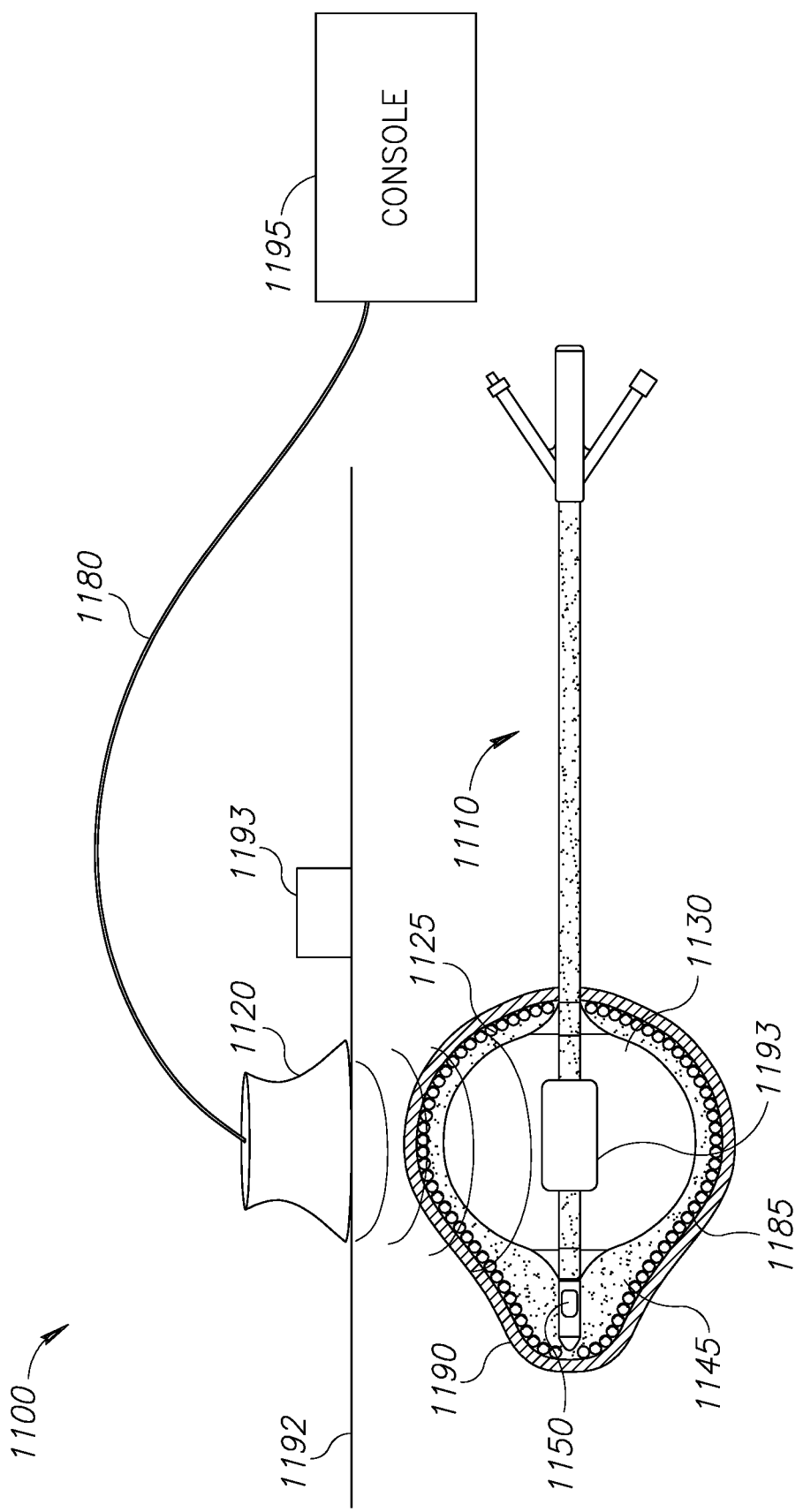
FIG. 11A shows a top view and partially transparent of an exemplary implementation of the system of FIG. 9, in accordance with another embodiment.
Figure 11B:
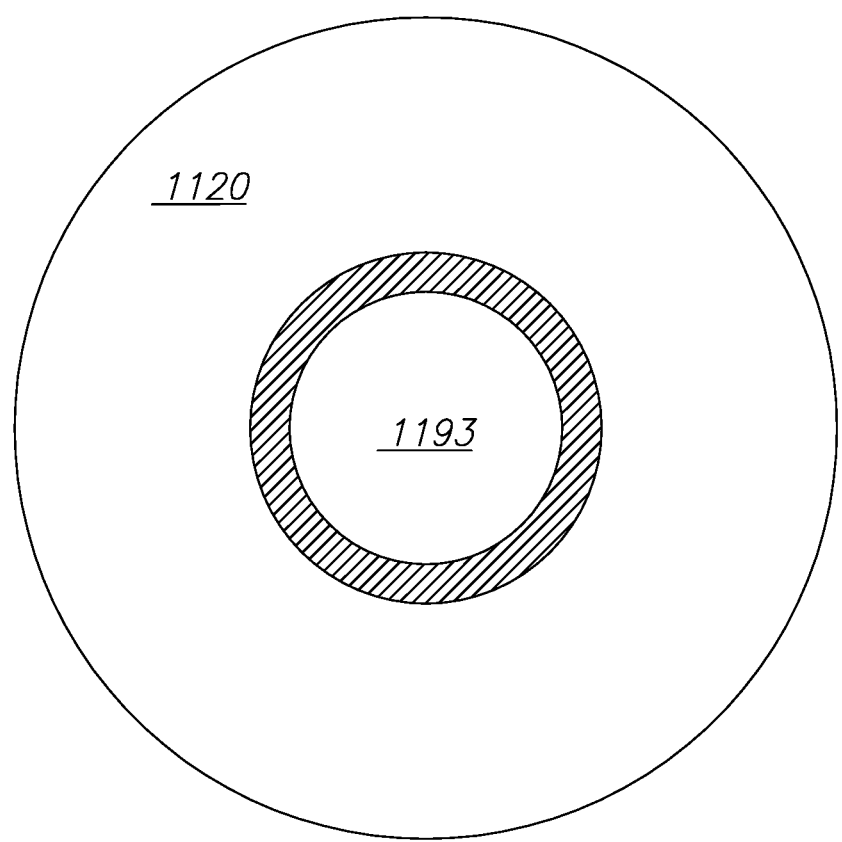
FIG. 11B is a schematic view showing emitting surface of an ultrasound transducer, in accordance with an embodiment.

Referring to the drawings, FIG. 11A shows a system 1100 disposed within urinary bladder 1190, in accordance with an embodiment. System 1100 is substantially similar to system 900 with the notable difference that a balloon 1130 corresponding to balloon 930 of FIG. 9 is filled with gas rather than acoustic coupling medium. A detector transducer 1193, corresponding to detector transducer 993 of FIG. 9, is positioned externally to urinary bladder 1190, rather than disposed within balloon 1130. Optionally, detector transducer 1193 may be a separate ultrasound transducer, or a part of an ultrasound transducer 1120, corresponding to ultrasound transducers 920 of FIG. 9, which applies the cavitation. Reference is now made to FIG. 11B which shows a schematic view of an emitting surface of an ultrasound transducer 1120 (e.g., HIUT) which comprises a detector transducer 1193 (e.g., PCD)

Figure 12:
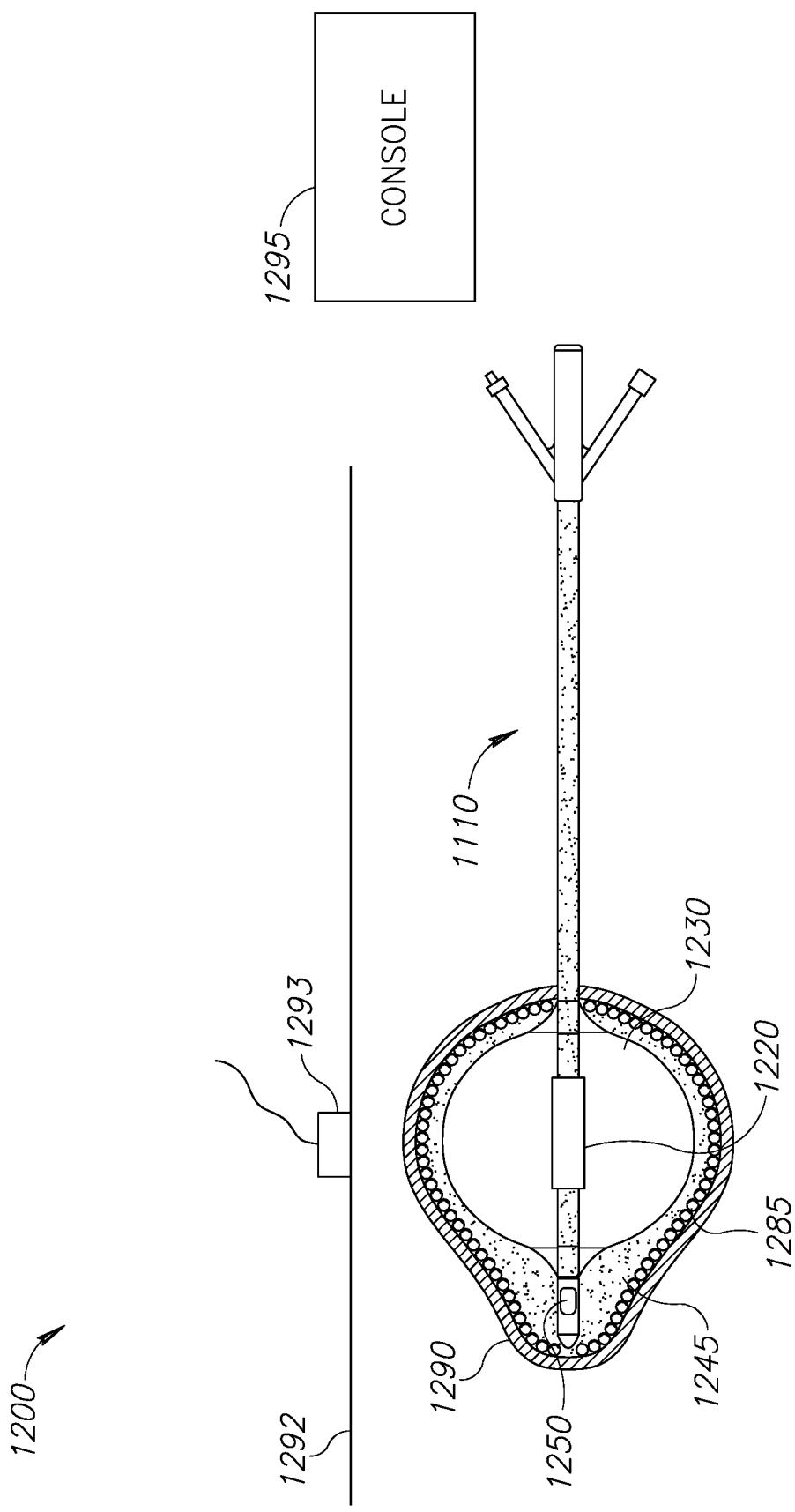
FIG. 12 shows a top view and partially transparent of an exemplary implementation of the system of FIG. 9, in accordance with another embodiment.

Reference is now made to FIG. 12 which shows a system 1200 disposed within urinary bladder 1290, in accordance with an embodiment. System 1200 is substantially similar to system 900 of FIG. 9, with the notable difference that an ultrasound transducer 1220, corresponding to ultrasound transducer 920 of FIG. 9, and a detector transducer 1293, corresponding to detector transducer 993 of FIG. 9 are arranged differently than in system 900 of FIG. 9. Ultrasound transducer 1220 is installed at a distal part of a catheter 1210 and a detector transducer 1293, is placed externally on the abdomen. Optionally a balloon 1230, corresponding to balloon 930 of FIG. 9, is filled with degassed liquid.

Figure 13:
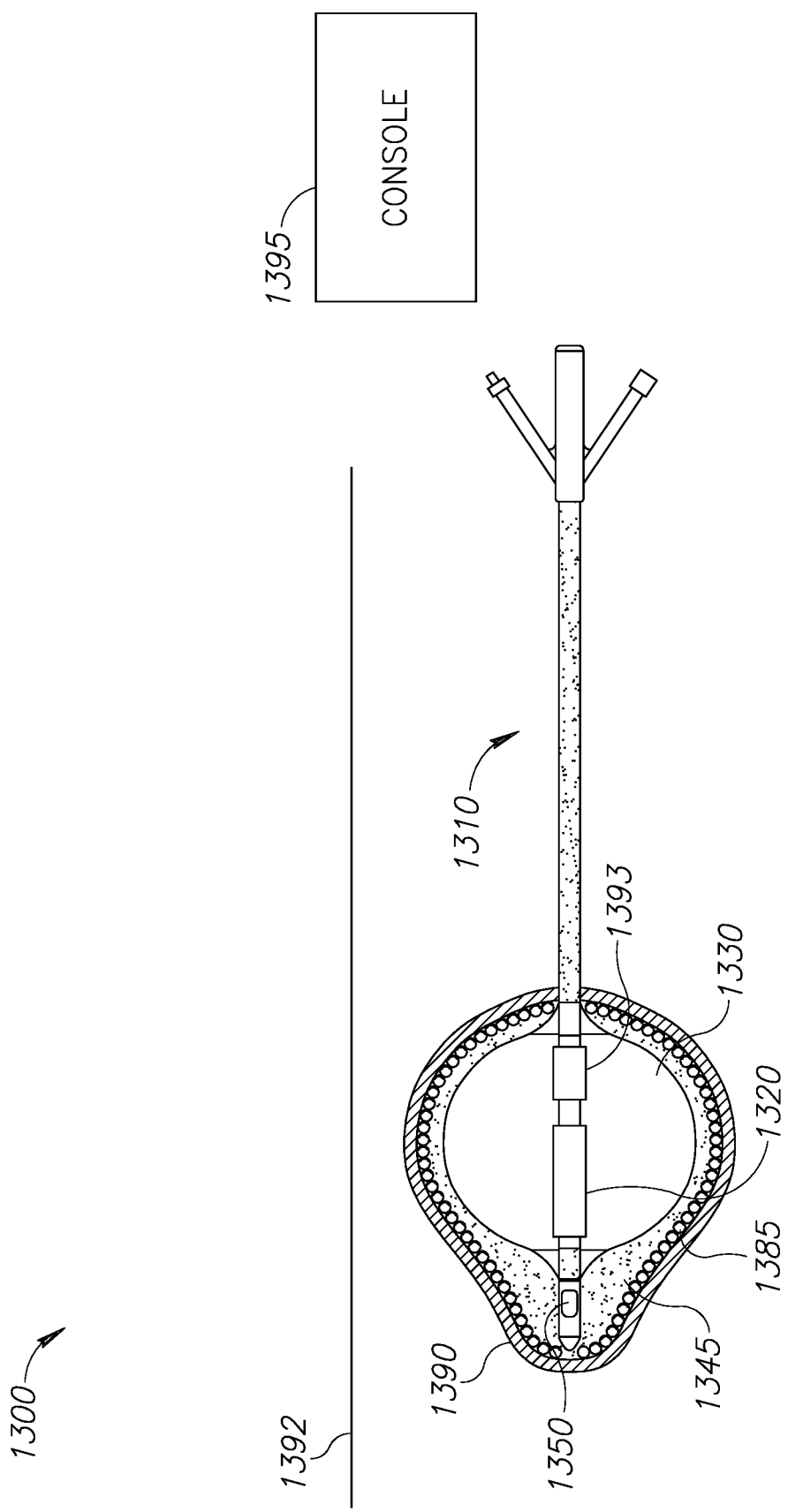
FIG. 13 shows a top view and partially transparent of an exemplary implementation of the system of FIG. 9, in accordance with another embodiment.

Reference is now made to FIG. 13 which shows a system 1300 disposed within urinary bladder 1390. System 1300 is substantially similar to system 900 of FIG. 9, with the notable difference that 1320, corresponding to ultrasound transducer 920 of FIG. 9, and a detector transducer 1393, corresponding to detector transducer 993 of FIG. 9, are placed on a distal part of a catheter of a catheter 1210, corresponding to catheter 910 of FIG. 9. Optionally a balloon 1330, corresponding to balloon 930 of FIG. 9, is filled with degassed liquid.

Reference is now made to FIGS. 12 and 13A-13C. FIG. 12 shows a flowchart of a method for delivering a therapeutic fluid to the urinary bladder, constructed and operative in accordance with an embodiment of the disclosed technique. FIG. 13A shows the device of FIG. 1 when inserted into the urinary bladder, according to the method of FIG. 12. FIG. 13B shows the device of FIG. 1 when inflated inside the urinary bladder and therapeutic fluid is delivered to the urinary bladder, according to the method of FIG. 12. FIG. 13C shows the device of FIG. 1 when ultrasonic waves are applied to the urinary bladder and cavitation of the therapeutic fluid is formed, according to the method of FIG. 12.

Figure 15A:
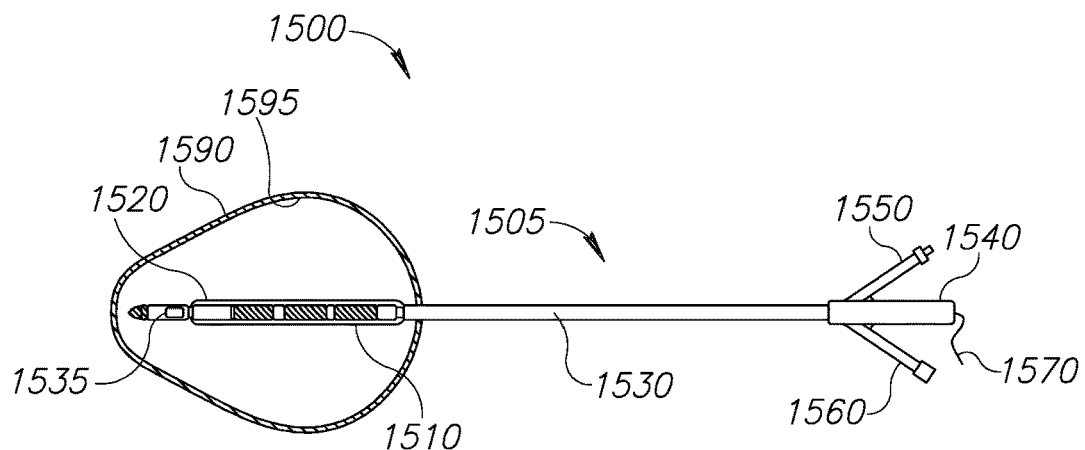
FIG. 15A shows the device of FIG. 1 when inserted into the urinary bladder, according to the method of FIG. 14.

In a step 1400, a distal portion of a urinary catheter and at least one ultrasonic transducer disposed thereabout is inserted into the urinary bladder. The at least one ultrasonic transducer may be enclosed by a balloon. The urinary catheter, the transducer and the balloon may be according to the urinary catheters, the transducers and the balloons disclosed herein such as catheter 110, transducers 120 and balloon 130 of device 100 of FIG. 1. With Reference to FIG. 15A, a device 1500 which includes a urinary catheter 1505 (or simply 'catheter 1505'), ultrasonic transducers 1510 (or simply 'transducers 1510') enclosed by a balloon 1520 is inserted into a urinary bladder 1590 (or simply 'bladder 1590'). A distal portion of device 1500 and catheter 1305 is placed in bladder 1590 and such that transducers 1510 and balloon 1520 are positioned in bladder 1590. Balloon 1520 is entirely or mostly deflated at this stage.

In a step 1410, the balloon may be inflated with an acoustic coupling medium via a first opening and a first longitudinal lumen of the urinary catheter. The first opening is disposed in the first longitudinal lumen and inside said balloon. The acoustic coupling medium may be a cold acoustic coupling medium. Alternatively, the acoustic coupling medium may be cooled in a further optional step. With reference to FIG. 15A, the acoustic coupling medium may be inserted into balloon 1520 via a first longitudinal lumen of catheter 1505 (not shown) and a first opening in the first longitudinal lumen (not shown). The first opening may be disposed inside balloon 1520. In a further optional step, the acoustic coupling medium may be continuously or intermittently circulated via an inlet channel 1550 and an outlet channel 1560. One of inlet channel 1550 and outlet channel 1560 may be the first longitudinal lumen and may include the first opening while the other may be a third longitudinal lumen (not shown) and may include a third opening (not shown) of catheter 1505 disposed in the third longitudinal lumen and inside balloon 1520.

Figure 15B:
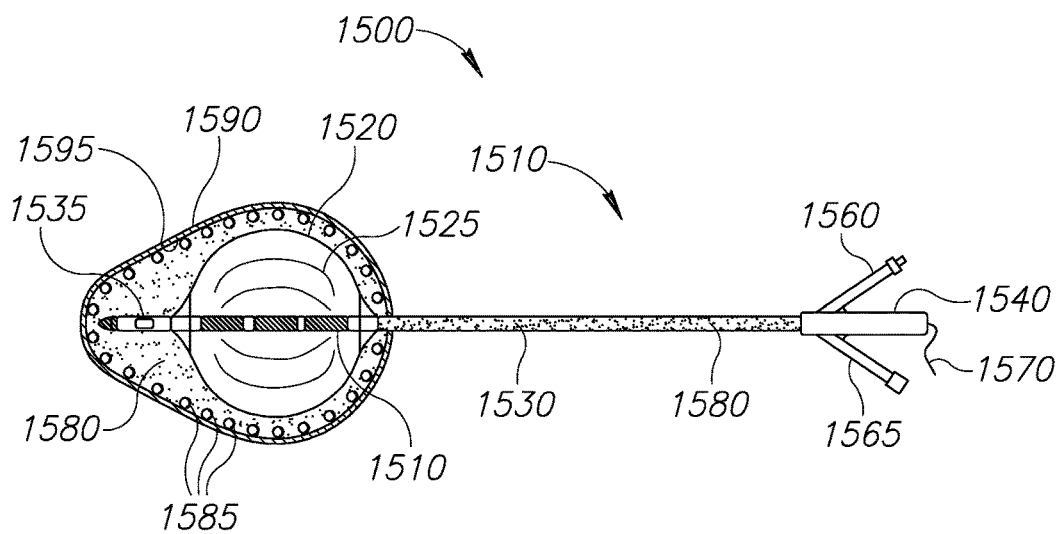
FIG. 15B shows the device of FIG. 1 when inflated within the urinary bladder and therapeutic fluid is introduced to the urinary bladder, according to the method of FIG. 14.

In a step 1420, therapeutic fluid may be delivered to the urinary bladder, around the balloon and via a second longitudinal lumen and a second opening of the urinary catheter. The second opening may be disposed in the second longitudinal lumen and outside of the balloon. The therapeutic fluid may or may not include a therapeutic agent to be delivered a tissue of the urinary bladder. With Reference to FIG. 15B, balloon 1520 is now inflated with the acoustic coupling medium within bladder 1590. A therapeutic fluid (not shown) is inserted to bladder 1590 (i.e., to the cavity formed between balloon 1520 and internal surface 1595 of bladder 1590). The therapeutic fluid may be inserted via a main channel 1540 of catheter 1505, through a second longitudinal lumen 1530 of catheter 1505 and into bladder 1590 via a second opening 1535 in second longitudinal lumen 1530. Second opening 1535 is disposed in the distal portion of catheter 1505 and outside balloon 1520. The therapeutic fluid includes a therapeutic agent 1580 which thus may be dispersed in bladder 1590. Optionally, the therapeutic agent is not included within the therapeutic fluid.

In an optional step, matter which encourages cavitation may be added to the therapeutic fluid. Such matter may be for example, contrast agents, such as microbubbles (e.g., Definity®, Optison® and SonoVue®) or gas, such as high concentration of gases (e.g., argon). Optionally, the gasses are inert gasses.

Figure 15C:
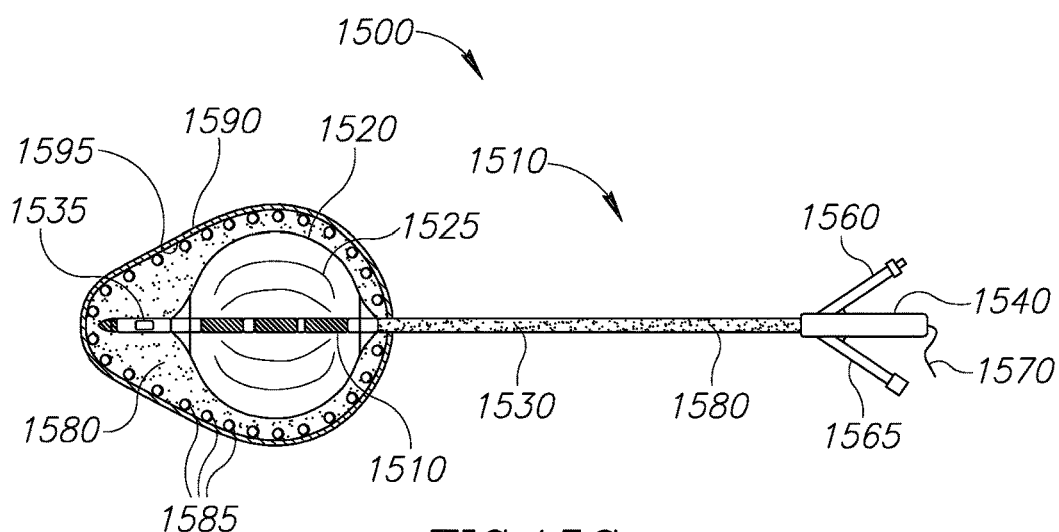
FIG. 15C shows the device of FIG. 1 when ultrasonic waves are applied to the urinary bladder and cavitation of the therapeutic fluid is formed, according to the method of FIG. 14.

In a step 1430, the at least one ultrasonic transducer may be activated to transmit ultrasonic waves towards an internal surface of the urinary bladder, to form cavitation bubbles in the therapeutic fluid adjacent to the internal surface. Little or no cavitation bubbles may be formed in the acoustic coupling medium in the balloon. By that, the permeability of the urinary bladder may be increased and the delivery of the therapeutic agent to tissue of the urinary bladder may be facilitated. The transducers may be activated continuously or intermittently. With reference to FIG. 15C, transducers 1510 may be activated to produce ultrasonic waves 1515. Cavitation bubbles 1585 may be formed in the therapeutic fluid, which fills the space between balloon 1520 and the bladder internal surface 1595, thereby bringing cavitation effects closer to the bladder internal surface 1595. Since balloon 1520 encloses transducers 1510 and since balloon 1520 is filled with an acoustic coupling medium, little or no cavitation bubbles may be formed balloon 1520 and in adjacent to ultrasonic transducers 1510. Optionally, the therapeutic agents may be added to the therapeutic fluid following formation of cavitation bubbles 1585. The therapeutic agent may be added within 0.01 second to 12 hours following activation of the at least one ultrasonic transducer. Optionally, the therapeutic agent may be added, 0.1 second to 10 minutes, 1 second to 10 minutes, 1 second to 30 minutes, 1 minute to 30 minutes, 1 minute to 60 minutes, 30 minutes to 60 minutes, 1 hour to 2 hours, 1 hour to 3 hours, or 1 hour to 6 hours following activation of the at least one ultrasonic transducer. Optionally, steps 1420 and 1430 may be performed simultaneously. Alternatively step 1420 may be performed sequentially. Optionally step 1420 may follow step 1430. Alternatively, step 1430 may follow step 1420, accordingly the therapeutic agent may be added following activation of the at least one ultrasonic transducer.

The ultrasonic transducers may be activated at intensity between 0.0009 and 16.5 Watts per square centimeter in order to facilitate the delivery of the therapeutic solution. In some embodiments, the ultrasonic transducers may be activated at intensity between 0.01 and 7.5 Watts per square centimeter. In some embodiments, the ultrasonic transducers may be activated at intensity between 7.5 and 15 Watts per square centimeter. In some embodiments, the ultrasonic transducers may be activated at intensity between 5 and 10 Watts per square centimeter. In some embodiments, the ultrasonic transducers may be activated at intensity between 12 and 15 Watts per square centimeter. In some embodiments, the ultrasonic transducers may be activated at intensity between 0.01 and 4 Watts per square centimeter.

The ultrasonic transducers may be activated at a frequency between 0.018 and 11 Megahertz. In some embodiments, the ultrasonic transducers may be activated at a frequency between 0.02 and 5 Megahertz. In some embodiments, the ultrasonic transducers may be activated at a frequency between 5 and 10 Megahertz. In some embodiments, the ultrasonic transducers may be activated at a frequency between 3 and 7 Megahertz. In some embodiments, the ultrasonic transducers may be activated at a frequency between 0.02 and 3 Megahertz. In some embodiments, the ultrasonic transducers may be activated at a frequency between 8 and 10 Megahertz.

In an optional step, the catheter may be rotated in a predefined angular measure and such that different peripheral portions of the distal portion of the catheter and/or of the balloon enclosing it may face different portions of the internal surface of the bladder. The transducers may be then activated again (i.e., in case the transducers are not activated continuously). This step may be performed iteratively, for example, such that specific peripheral portion of the catheter and/or of the balloon may each time face a different portion of the internal surface of the bladder. This step may be applicable, for example, when an asymmetric balloon is used and/or when a portion of the balloon touches the internal surface of the bladder. Thus, several circles of treatment may be applied, for example, in order to treat the entire bladder. When the catheter is multiply rotated, it may be rotated each time in a fixed predefined angle or at various predefined angles.

In an optional step 1440, therapeutic agent may be delivered to the urinary bladder. This step may be taken in cases where the therapeutic solution which was delivered to the urinary bladder according to step 1420 does not include the therapeutic agent. Since ultrasound effect of increasing tissue permeability may last for many hours following ultrasound treatment, the bladder may be first ultrasonically irradiated with ultrasound to form cavitation effects in the delivered therapeutic solution and only then washed with the therapeutic agent.

Figure 14:
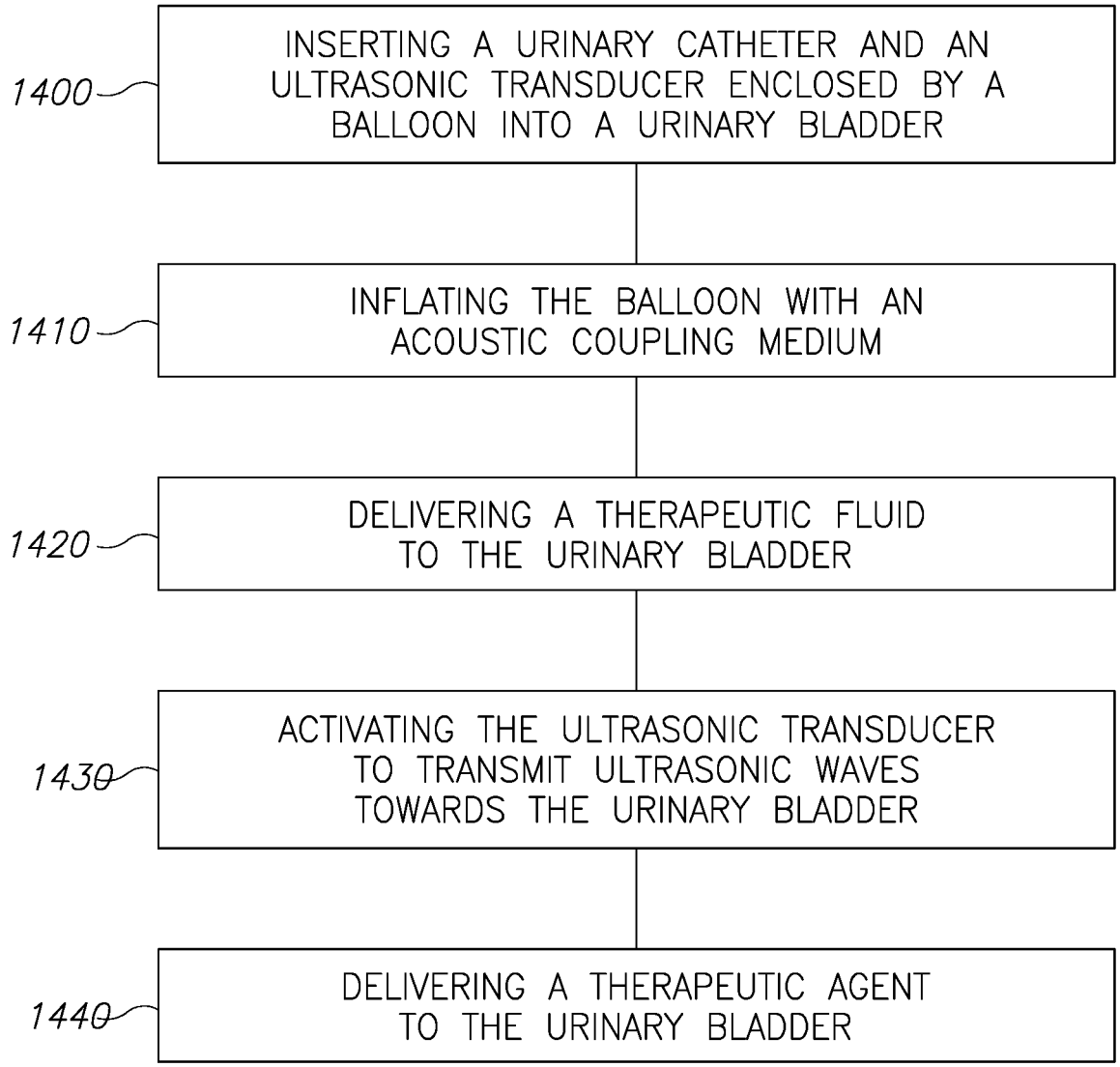
FIG. 14 shows a flowchart of a method for delivering a therapeutic fluid to a urinary bladder, constructed and operative in accordance with an embodiment of the disclosed technique.

The disclosed devices and kits may be operated according to the method of FIG. 14.

When a value is defined herein as a range between two numbers, the value may be equal to any number between these two numbers or to each of these two numbers.

Control unit 997 may include one or more software modules to perform any of the controlling, computing, receiving and/or transmitting functions described herein.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A kit comprising:
   a urinary catheter comprising first and second longitudinal lumens;
   a balloon mounted on said urinary catheter at a distal portion thereof;
   at least one ultrasonic transducer disposed on said urinary catheter within said balloon; and
   a reservoir comprising an acoustic coupling medium that does not favor cavitation, in fluid connection with said first longitudinal lumen,
   wherein said urinary catheter further comprises a first opening in said first longitudinal lumen, said first opening disposed inside said balloon and configured to inflate said balloon with said acoustic coupling medium that does not favor cavitation, and
   wherein said urinary catheter further comprises a second opening in said second longitudinal lumen, said second opening disposed outside said balloon.

2. The kit according to claim 1, wherein said at least one ultrasonic transducer is structured to produce an unfocused, diverging acoustic field.

3. The kit according to claim 1, wherein said balloon comprises bulges configured to distance said balloon from a bladder wall.

4. The kit of claim 1, wherein said at least one ultrasonic transducer/detector is adapted for a working frequency in the range of 150 Kilohertz to 200 Kilohertz.

5. The kit of claim 1, wherein said at least one ultrasonic transducer/detector is configured to resonate at a frequency between 36 Kilohertz and 100 Kilohertz.

6. The kit of claim 1, wherein said at least one ultrasonic transducer is configured to resonate at a frequency between 36 Kilohertz and one Megahertz and at a frequency above one Megahertz.

7. The kit of claim 1, wherein said balloon, when inflated in a urinary bladder having an internal surface, is adapted to contact a trigone of the urinary bladder and thereby prevent delivery of any fluid dispensed through said second opening of said second lumen to the trigone of the urinary bladder, without preventing delivery of any said fluid to other parts of the internal surface of the urinary bladder when in use.

8. The kit of claim 1, further including a cavitation detector adapted for monitoring cavitation levels and for setting a power output of said at least one ultrasonic transducer according to the monitored cavitation levels.

9. The kit of claim 1, wherein said acoustic coupling medium that does not favor cavitation is a degassed solution.

10. The kit of claim 1, wherein said balloon, once inflated, has: sections that inflate to different sizes having differing diameters.

11. The kit of claim 10, wherein said balloon, once inflated, comprises a shape of an elongated cylinder having two lateral portions and a middle portion, wherein said two lateral portions are larger in diameter than a diameter of said middle portion.

12. The kit of claim 1, further including a second reservoir comprising a therapeutic fluid, in fluid connection with said second longitudinal lumen.

13. The kit according to claim 12, wherein said therapeutic fluid comprises a cavitation booster selected from the group consisting of an ultrasound contrast agent, micro-particles, nanoparticles, liposomes, and a gas.

14. The kit according to claim 12, wherein said therapeutic fluid comprises one or more therapeutic agents selected from the group consisting of a drug, a chemotherapeutic agent, a tracer, a marker, a radioactive compound, a small molecule, and a gene.

15. The kit according to claim 14, wherein said one or more therapeutic agents are selected from the group consisting of anti muscarinic agents, anticholinergic agents, anesthetic agents, and botulinum toxin.

16. The kit according to claim 14, wherein said one or more therapeutic agents are selected from the group consisting of Bacillus Calmette Guerin (BCG) vaccine, cisplatin, doxorubicin, valrubicin, gemcitabine, mycobacterial cell wall-DNA complex (MCC), methotrexate, vinblastine, thiotepa, mitomycin, fluorouracil, leuprolide, diethylstilbestrol, estramustine, megestrol acetate, cyproterone, flutamide, a selective estrogen receptor modulator, toxin, cyclophosphamide, and any combination thereof.

17. A method for delivering a therapeutic fluid to a urinary bladder having an internal surface, using the kit of claim 1, the method comprising: inserting the distal portion of said urinary catheter, including said balloon, into the urinary bladder, inflating said balloon with said acoustic coupling medium that does not favor cavitation, via said first longitudinal lumen and said first opening of said urinary catheter, delivering to the urinary bladder, between said inflated balloon and the internal surface of the urinary bladder, therapeutic fluid introduced via said second longitudinal lumen and said second opening of said urinary catheter, and activating said at least one ultrasonic transducer to transmit ultrasonic waves towards the internal surface of the urinary bladder, to form cavitation bubbles in said therapeutic fluid adjacent to the internal surface of the urinary bladder and little or no cavitation bubbles in said acoustic coupling medium that does not favor cavitation, in said balloon.

18. The method according to claim 17, wherein said therapeutic fluid comprises (a) a cavitation booster selected from the group consisting of an ultrasound contrast agent, micro-particles, nano-particles and a gas; (b) botulinum toxin, or (c) a combination thereof.

19. The method according to claim 17, wherein said at least one ultrasonic transducer is structured to produce an unfocused, diverging acoustic field.

20. The method according to claim 17, wherein said at least one ultrasonic transducer is selected from the group consisting of (a) at least one tubular transducer surrounding a section of said urinary catheter, and (b) a plurality of flat, rectangular transducers arranged around a section of said urinary catheter.

21. The method according to claim 17, further comprising rotating at least said at least one ultrasonic transducer when said at least one ultrasonic transducer is activated.

22. The method of claim 17, wherein said balloon, once inflated, comprises a shape of an elongated cylinder having two lateral portions and a middle portion, wherein said two lateral portions are larger in diameter than a diameter of said middle portion, said two lateral portions being adapted to contact the internal surface of the urinary bladder, allowing said therapeutic fluid to flow or reside therebetween, in a space formed between the middle portion of the elongated cylinder and the internal surface of the urinary bladder.

23. The method of claim 17, wherein said insertion step places said urinary catheter in a position within the urinary bladder such that said balloon, once inflated, will not contact the internal surface of the urinary bladder.

24. The method of claim 17, wherein said balloon is shaped such that, when inflated in the urinary bladder, said balloon contacts only areas of the internal surface of the urinary bladder where cavitation is not desired and thereby prevents delivery of said therapeutic fluid to said areas, without preventing delivery of said therapeutic fluid to the rest of the internal surface of the urinary bladder when in use.

25. The method of claim 17, wherein said acoustic coupling medium that does not favor cavitation is a degassed solution.

\* \* \* \* \*